US012685757B2

(12) United States Patent
Ahern et al.

(10) Patent No.: US 12,685,757 B2
(45) Date of Patent: Jul. 21, 2026

(54) METHOD TO INCREASE SYSTEMIC BLOOD PRESSURE IN SHOCK

(71) Applicant: GEORGETOWN UNIVERSITY, Washington, DC (US)

(72) Inventors: Gerard P. Ahern, Washington, DC (US); Thieu X. Phan, Washington, DC (US)

(73) Assignee: GEORGETOWN UNIVERSITY, Washington, DC (US)

(*) Notice: Subject to any disclaimer, the term of this patent is extended or adjusted under 35 U.S.C. 154(b) by 1130 days.

(21) Appl. No.: 17/636,751

(22) PCT Filed: Aug. 20, 2020

(86) PCT No.: PCT/US2020/047172
§ 371 (c)(1),
(2) Date: Feb. 18, 2022

(87) PCT Pub. No.: WO2021/035037
PCT Pub. Date: Feb. 25, 2021

(65) Prior Publication Data

US 2022/0288164 A1 Sep. 15, 2022

Related U.S. Application Data

(60) Provisional application No. 62/889,344, filed on Aug. 20, 2019.

(51) Int. Cl.

| | |
|---|---|
| ***A61K 38/00*** | (2006.01) |
| ***A61K 31/137*** | (2006.01) |
| ***A61K 31/165*** | (2006.01) |
| ***A61K 31/357*** | (2006.01) |
| ***A61K 31/662*** | (2006.01) |
| ***A61K 38/08*** | (2019.01) |
| ***A61K 38/17*** | (2006.01) |
| ***A61P 9/12*** | (2006.01) |

(52) U.S. Cl.
CPC ........ *A61K 38/1767* (2013.01); *A61K 31/137* (2013.01); *A61K 31/165* (2013.01); *A61K 31/357* (2013.01); *A61K 31/662* (2013.01); *A61K 38/085* (2013.01); *A61P 9/12* (2018.01)

(58) Field of Classification Search
CPC ...... A61K 38/1767; A61K 38/085; A61P 9/12
See application file for complete search history.

(56) References Cited

U.S. PATENT DOCUMENTS

| | | | | |
|---|---|---|---|---|
| 2010/0292755 A1* | 11/2010 | Jones | ........................ | A61P 9/10 607/46 |
| 2016/0045494 A1* | 2/2016 | Chance | ................ | G01N 33/573 514/254.02 |
| 2016/0128933 A1* | 5/2016 | Shang | .................. | A61K 31/125 514/703 |
| 2017/0196931 A1* | 7/2017 | Chawla | ..................... | A61P 9/02 |

OTHER PUBLICATIONS

Dellinger et al., Surviving Sepsis Campaign Guidelines Committee including the Pediatric Subgroup. Surviving sepsis campaign: international guidelines for management of severe sepsis and septic shock: 2012. Crit Care Med. Feb. 2013;41(2):580-637. (Year: 2013).*

"Mean Arterial Pressure—Map," achieved Sep. 11, 2018 by the WayBack Machine (Year: 2018).*

* cited by examiner

*Primary Examiner* — Fred H Reynolds
*Assistant Examiner* — Sara E Konopelski Snavely
(74) *Attorney, Agent, or Firm* — BLANK ROME LLP

(57) ABSTRACT

Provided herein are methods of stabilizing blood pressure in severe sepsis/septic shock and other types of distributive shock using TRPV1 agonists. Also provided are pharmaceutical formulations for increasing blood pressure in septic shock the formulation including at least one TRPV1 agonist in a dosage form for parenteral administration, wherein the TRPV1 agonist is selected from capsaicin, daphnane TRPV1 agonists, vanillotoxin, N-oleoyl dopamine, N-arachidonyl dopamine, BrP-LPA, and derivatives and analogues thereof. Also provided are TRPV1 agonists co-lyophilized with adrenergic agonists and/or angiotensins in a dosage form for reconstitution and parenteral administration.

20 Claims, 20 Drawing Sheets

Specification includes a Sequence Listing.

HiK+
Diameter (μm)
WT
TRPV1-null
Time (s)

BCTC
HiK+
Time (s)

HiK+/Blue light (40 s)
Dilation (%)
WT
+BCTC
TRPV1-null
TRPV1-ChR2
T 1/2 for recovery tone (s)

Blue light

HiK+ (6 s)/Blue light (4 s)
60 25 60 60 (μm)

0 Ca2+

METHOD TO INCREASE SYSTEMIC BLOOD PRESSURE IN SHOCK

CROSS-REFERENCE TO RELATED APPLICATIONS

This application is a U.S. National Stage Application of International Application No. PCT/US2020/047172, filed on Aug. 20, 2020, which claims priority to U.S. Provisional Application Number 62/889,344, filed Aug. 20, 2019, both of which are hereby incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 13, 2025, is named 128503-00210_SL.txt and is 958 bytes in size.

FIELD OF THE INVENTION

This invention relates generally to the stabilization of blood pressure in shock.

BACKGROUND OF THE INVENTION

Without limiting the scope of the invention, its background is described in connection the consequences of shock and with existing treatments for hypotensive shock. Severe sepsis and septic shock are significant causes of morbidity and mortality and the most common cause of death among critically ill patients in non-coronary intensive care units. In the United States, there are approximately 850,000 cases of sepsis annually and the associated health care costs are approximately $20 billion per year. Globally, sepsis prevalence is even greater, particularly in low-income countries. Notably, despite treatment, the septic shock-associated mortality is 47% (Singer et al., "The Third International Consensus Definitions for Sepsis and Septic Shock (Sepsis-3)" *JAMA* 315(8) (2016) 801-810.

Severe sepsis is associated with hyper-inflammation hypotension and edema. Standard treatment for hypotensive shock includes vasoconstrictor drugs (adrenergic/dopamine agonists). However, in many patients these drugs lose their effectiveness. Moreover, these vasoconstrictors can compromise blood flow to vital organs, in particular the spleen and kidney, that are already impacted by sepsis.

Angiotensin II (GIAPREZA™) infusion is the newest treatment for blood pressure control during septic shock, approved by the FDA in 2017. However, angiotensin II (Ang II) impairs blood flow to the kidney and spleen and has pro-coagulant properties that exacerbate the coagulation risk already present in sepsis patients. Indeed, adverse thromboembolic events are reported in >10% of patients. Further, Ang II had relatively modest efficacy compared with placebo: death by day 28 occurred in 75 of 163 (46.0%) in the Ang II group compared with 85 of 158 (53.8%) in the placebo group (Khanna et al., "Angiotensisn II for the Treatment of Vasodilatory Shock" *NEJM*377 (2017) 419-430). Thus, there is clearly a need for better treatment options for severe sepsis.

BRIEF DESCRIPTION OF THE DRAWINGS

For a more complete understanding of the present invention, including features and advantages, reference is now made to the detailed description of the invention along with the accompanying figures:

FIG. 1A shows expression of TRPV1 in TRPV1 reporter mice and reveals TRPV1 expression in small arterioles of the ventricular myocardium where there is an analysis of whole hearts and transverse heart sections from TRPV1-Cre:tdTomato mice;

FIG. 2B is a graph of arterial maps of functional TRPV1 expression where there is TRPV1 expression (nLacZ staining) in forelimb arteries and muscle branches versus vessel diameter (n=4-6 arteries from 5 mice per group, *P<0.05, ***P<0.001); arterial color-coding (not shown) was applied;

FIG. 2C is an image which shows capsaicin (1 μM) evoked $Ca^{2+}$ responses in forelimb arteries of different diameter (n≥85-150 cells per group from 3 independent experiments, P<0.01, *P<0.001); arterial color-coding (not shown) was applied;

FIG. 2D is a graph which shows capsaicin (1 μM) evoked $Ca^{2+}$ responses in forelimb arteries of different diameter (n≥85-150 cells per group from 3 independent experiments, P<0.01, *P<0.001); arterial color-coding (not shown) was applied;

FIG. 2E is a graph which shows capsaicin (1 μM) evoked $Ca^{2+}$ responses in forelimb arteries of different diameter (n≥85-150 cells per group from 3 independent experiments, P<0.01, *P<0.001); arterial color-coding (not shown) was applied;

Figure 3A:
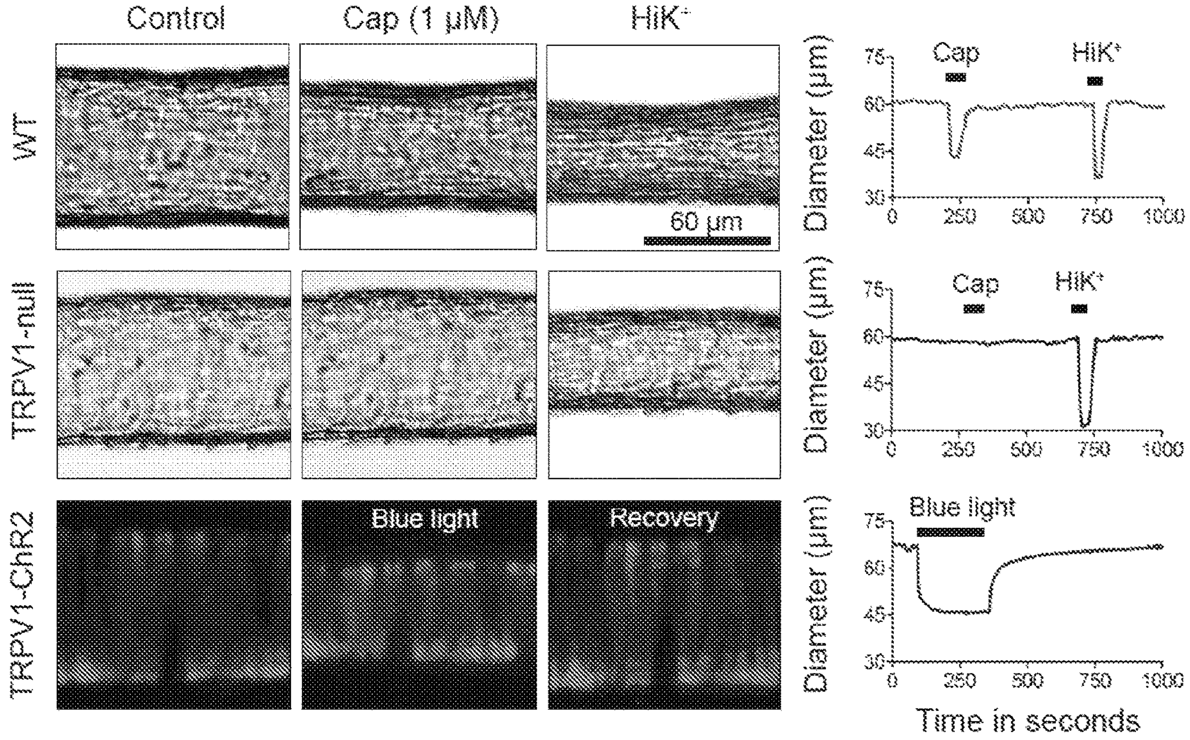
Figure 3B:
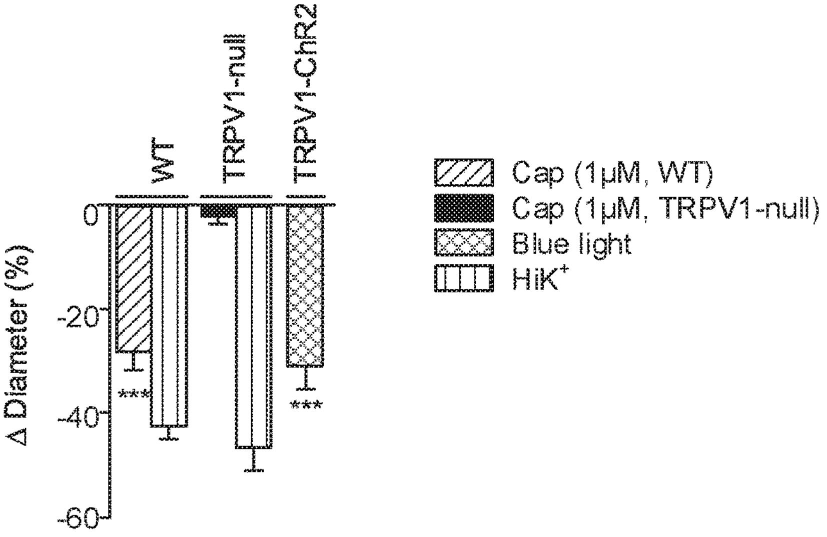
Figure 3C:
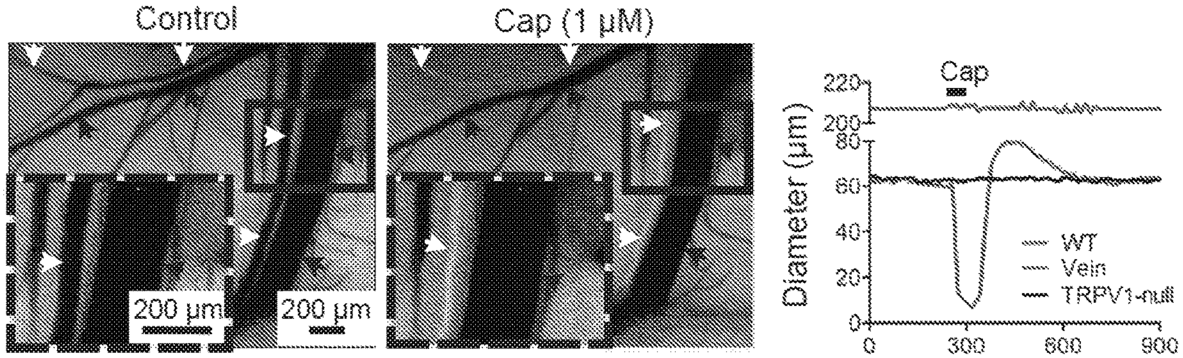
Figure 3D:
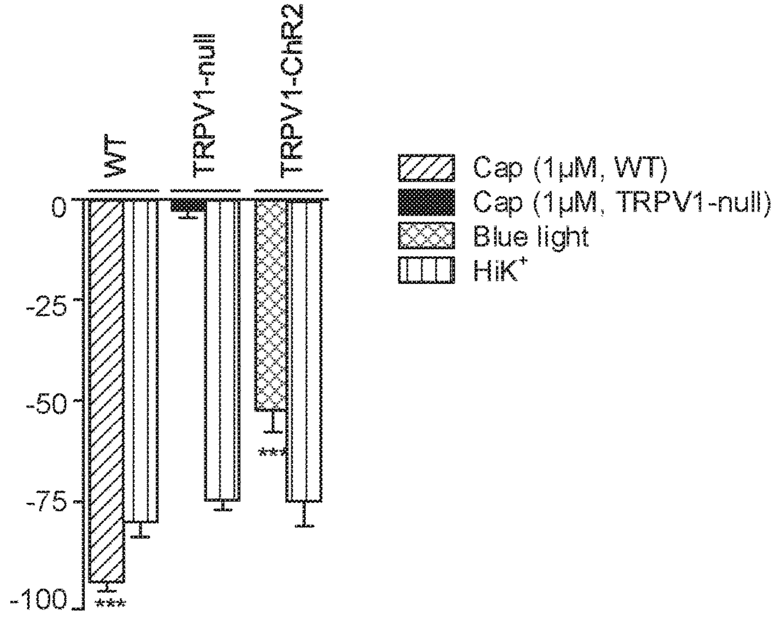

FIG. 3A-FIG. 3H show results of TRPV1 agonists and antagonists bi-directionally regulating arteriole tone FIG. 3A is a set of images and a graph which shows results of TRPV1 agonists and antagonists bi-directionally regulating arteriole tone demonstrating that capsaicin (1 μM) constricts isolated, pressurized (60 mmHg) arteries from wild-type but not TRPV1-null mice. Responses to 50 mM KCl are shown for comparison. Blue light irradiation constricts arteries from mice expressing Channelrhodopsin-2 (ChR2) under the control of the TRPV1 promoter (TRPV1-Cre:ChR2 mice) (n=4-7 arteries from 3-5 mice per group, ***P<0.001);

FIG. 3B is a graph which shows results of TRPV1 agonists and antagonists bi-directionally regulating arteriole tone demonstrating that capsaicin (1 μM) constricts isolated, pressurized (60 mmHg) arteries from wild-type but not TRPV1-null mice. Responses to 50 mM KCl are shown for comparison. Blue light irradiation constricts arteries from mice expressing Channelrhodopsin-2 (ChR2) under the control of the TRPV1 promoter (TRPV1-Cre:ChR2 mice) (n=4-7 arteries from 3-5 mice per group, ***P<0.001);

FIG. 3C is an image and graph which shows intravital imaging shows that capsaicin constricts radial arterioles (white arrowheads) without affecting veins (black arrowheads). The inset (dashed line) shows expanded view of the designated area (solid line). Arteries from TRPV1-null mice are unresponsive to capsaicin and blue-light constricts arteries from TRPV1-Cre:ChR2 mice (n=4-7 arteries from 3-5 mice per group, *P<0.001). FIG. 3E-FIG. 3H show that BCTC (1 μM) dilates isolated pressurized (60 mmHg) arterioles and in vivo arteries from WT but not TRPV1-null mice; (BCTC and $Ca^{2+}$ free dilation n≥3 arteries from 3 mice per group, *P<0.001);

FIG. 3D is a graph which shows intravital imaging shows that capsaicin constricts radial arterioles (white arrowheads) without affecting veins (black arrowheads). The inset (dashed line) shows expanded view of the designated area (solid line). Arteries from TRPV1-null mice are unresponsive to capsaicin and blue-light constricts arteries from TRPV1-Cre:ChR2 mice (n=4-7 arteries from 3-5 mice per group, ***P<0.001).

Figure 3E:
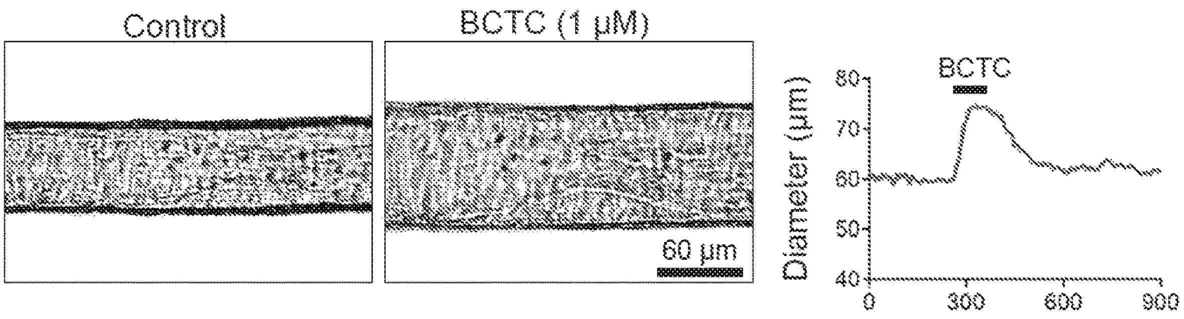
Figure 3F:
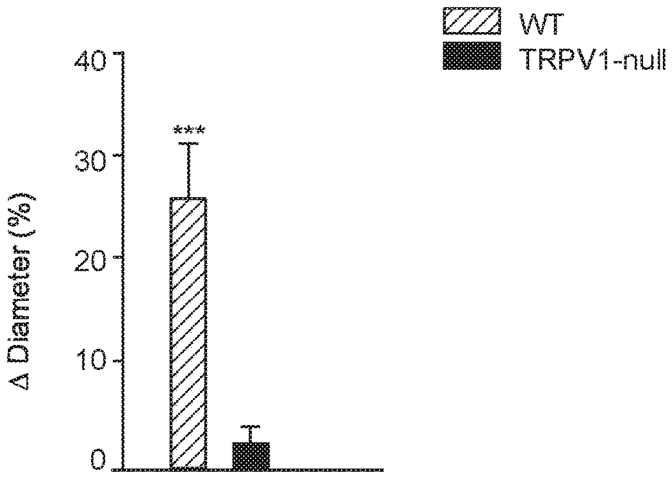
Figure 3G:
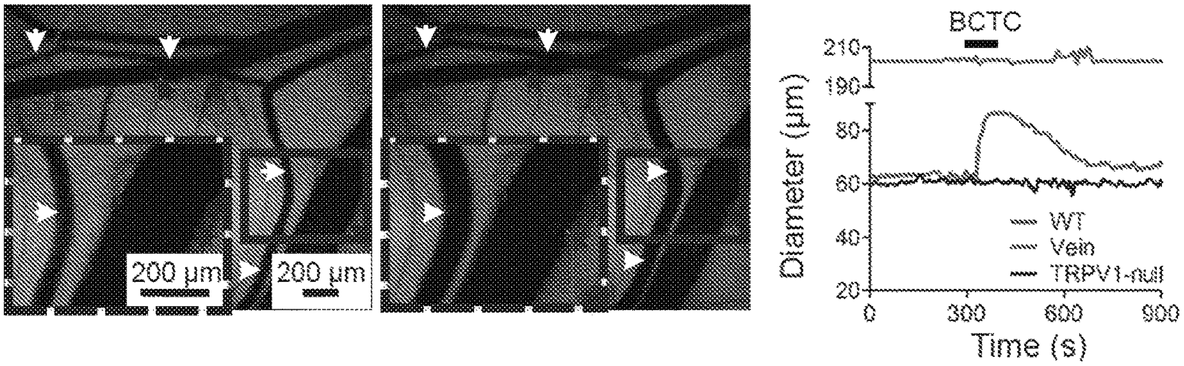
Figure 3H:
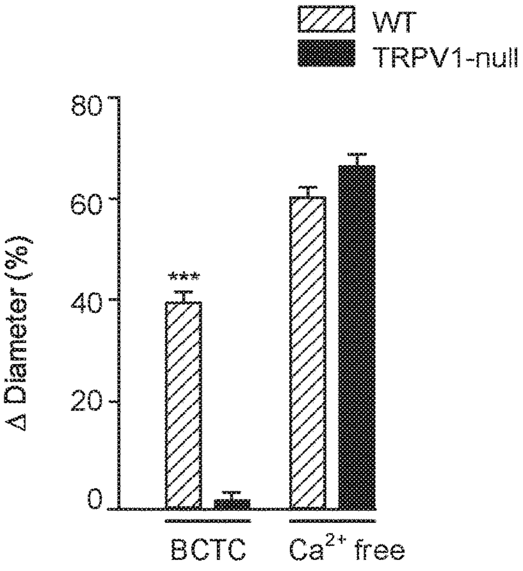
Figure 4A:
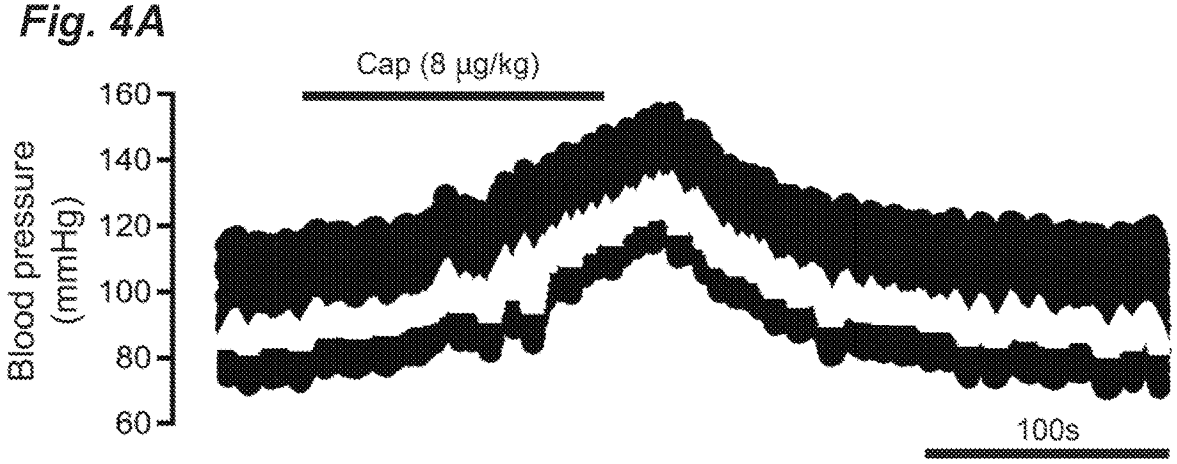
Figure 4B:
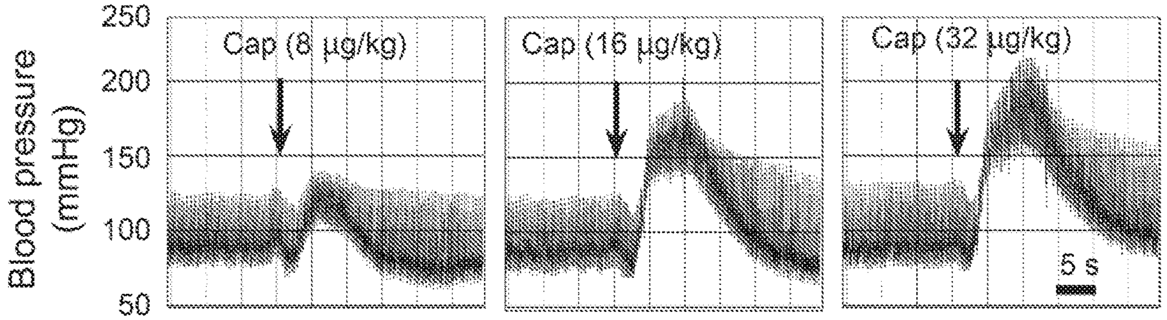
Figure 4C:
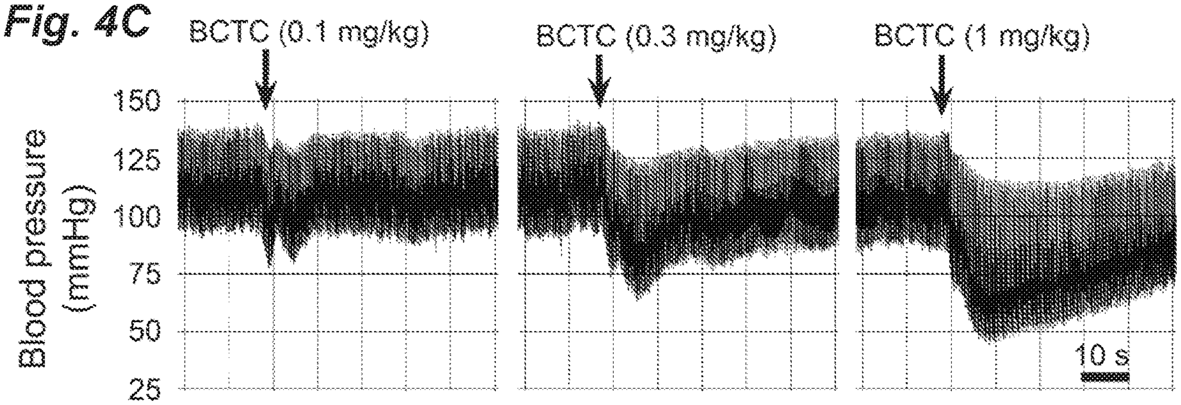

FIG. 3E is an image and graph which shows that BCTC (1 μM) dilates isolated pressurized (60 mmHg) arterioles and in vivo arteries from WT but not TRPV1-null mice; (BCTC and $Ca^{2+}$ free dilation n≥3 arteries from 3 mice per group, ***P<0.001);

FIG. 3F is a graph which shows that BCTC (1 μM) dilates isolated pressurized (60 mmHg) arterioles and in vivo arteries from WT but not TRPV1-null mice; (BCTC and $Ca^{2+}$ free dilation n≥3 arteries from 3 mice per group, ***P<0.001);

FIG. 3G is a set of images and a graph which shows that BCTC (1 μM) dilates isolated pressurized (60 mmHg) arterioles and in vivo arteries from WT but not TRPV1-null mice; (BCTC and $Ca^{2+}$ free dilation n≥3 arteries from 3 mice per group, ***P<0.001);

FIG. 3H is a graph which shows that BCTC (1 μM) dilates isolated pressurized (60 mmHg) arterioles and in vivo arteries from WT but not TRPV1-null mice; (BCTC and $Ca^{2+}$ free dilation n≥3 arteries from 3 mice per group, ***P<0.001);

FIG. 4A is a graph which presents data showing that TRPV1 regulates systemic blood pressure, demonstrating that intravenous infusion (IV; 2 min) of capsaicin increases systemic blood pressure in an anesthetized rat (mean arterial pressure is shown in the middle of the trace);

FIG. 4B is a set of graphs which presents data showing that TRPV1 regulates systemic blood pressure, demonstrating that bolus IV administration of capsaicin or BCTC in rats (pretreated with atropine) increases or decreases blood pressure, respectively in a dose-dependent manner;

FIG. 4C is a set of graphs which presents data showing that TRPV1 regulates systemic blood pressure, demonstrating that bolus IV administration of capsaicin or BCTC in rats (pretreated with atropine) increases or decreases blood pressure, respectively in a dose-dependent manner.

Figure 4D:
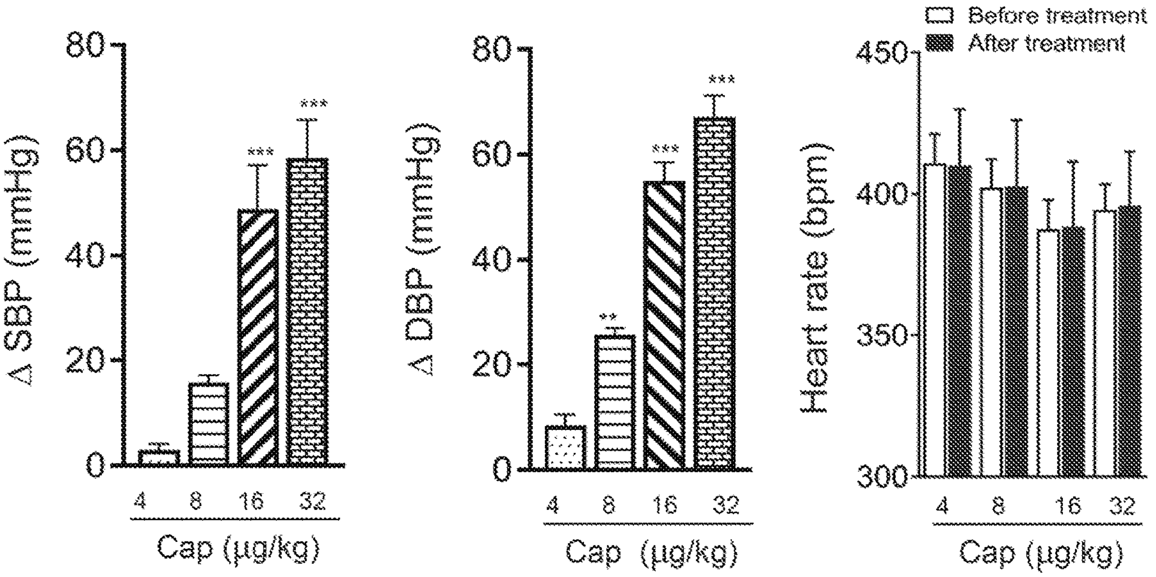
Figure 4E:
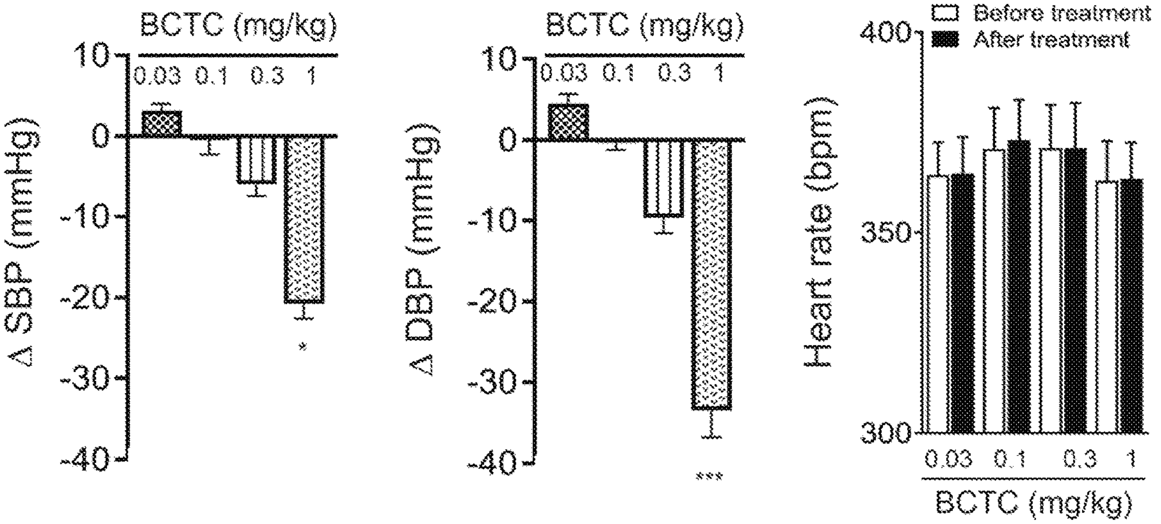
Figure 4F:
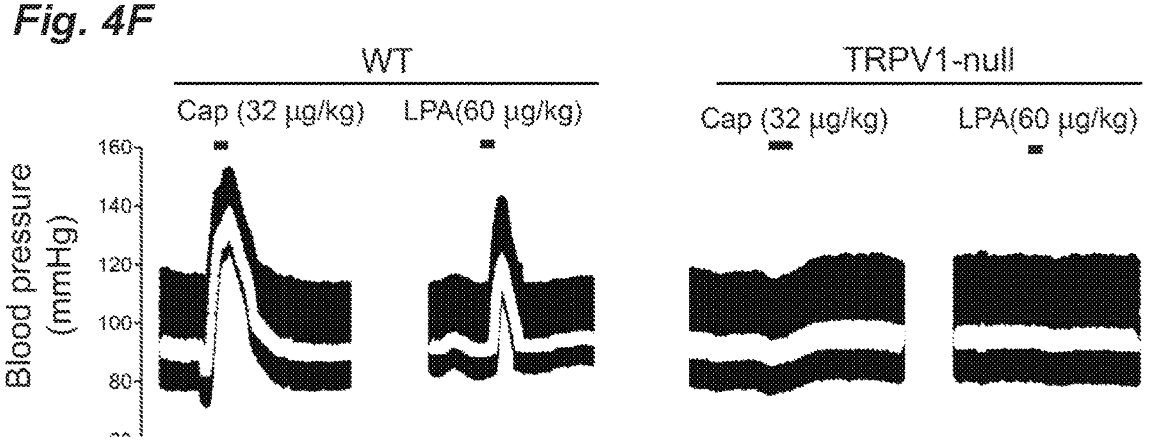
Figure 4G:
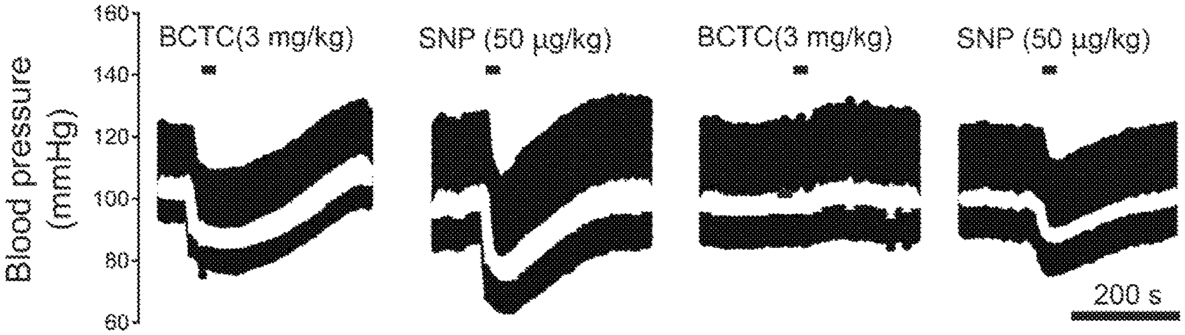
Figure 4H:
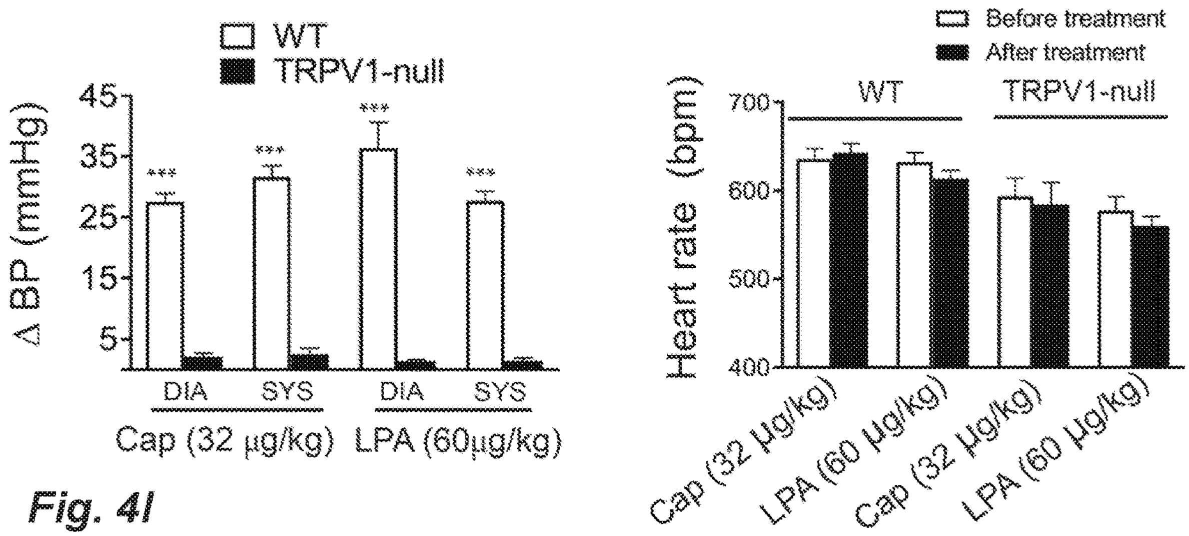
Figure 4I:
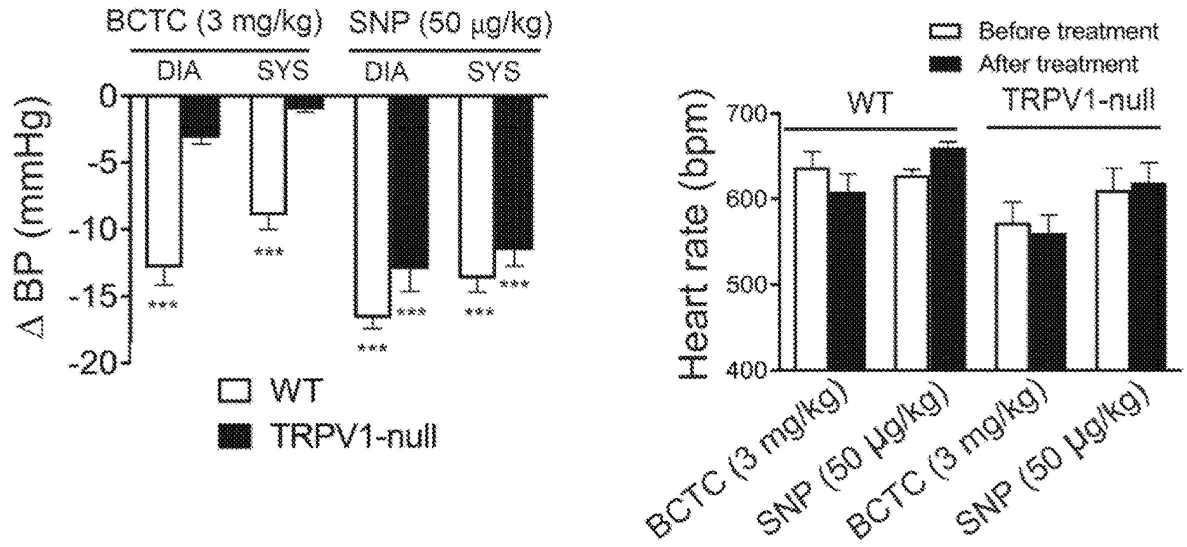
Figures 5A, 5B, 5C, 5D, 5E, 5F, 5G, 5H, 5I:
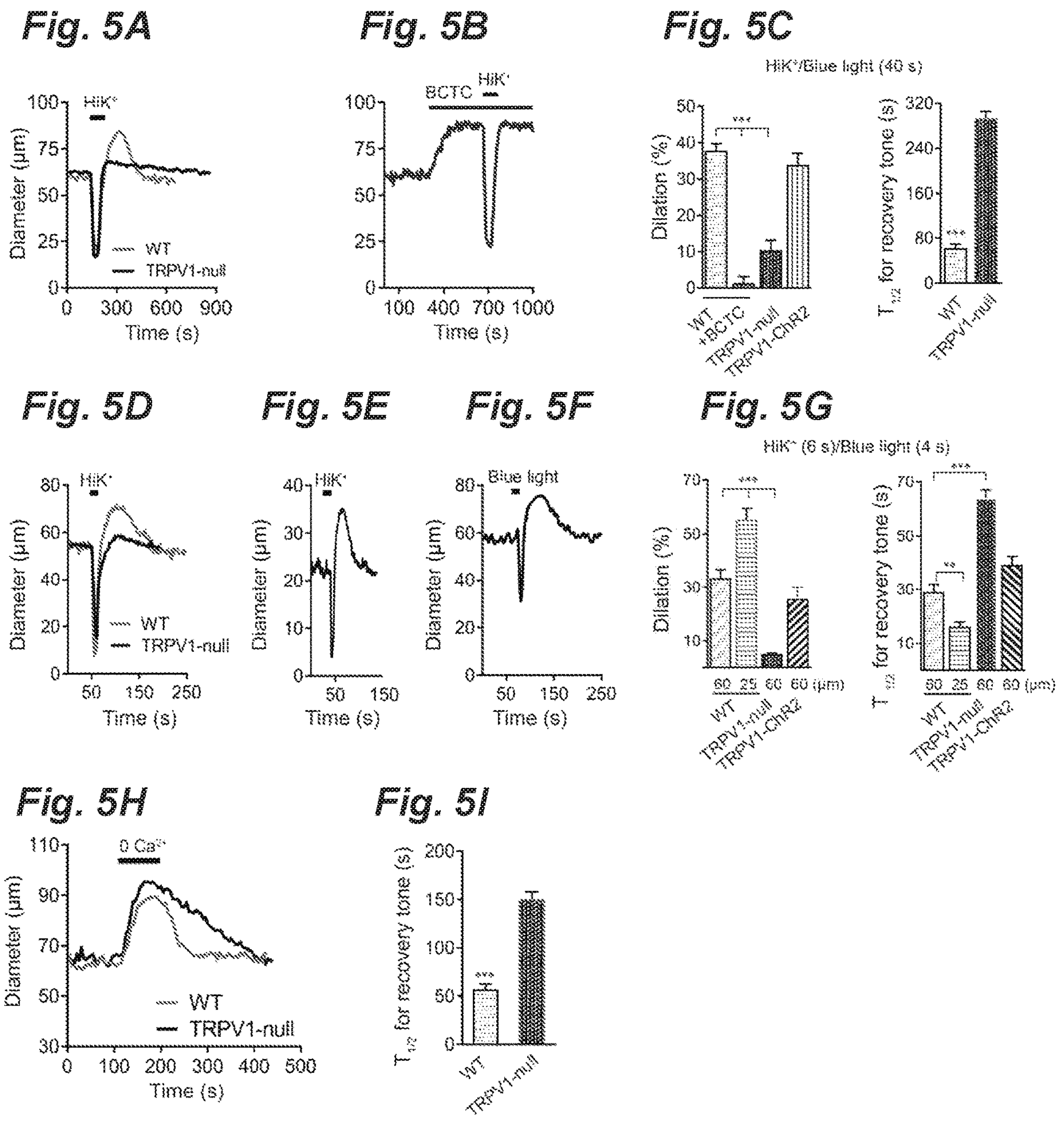
Figure 6A:
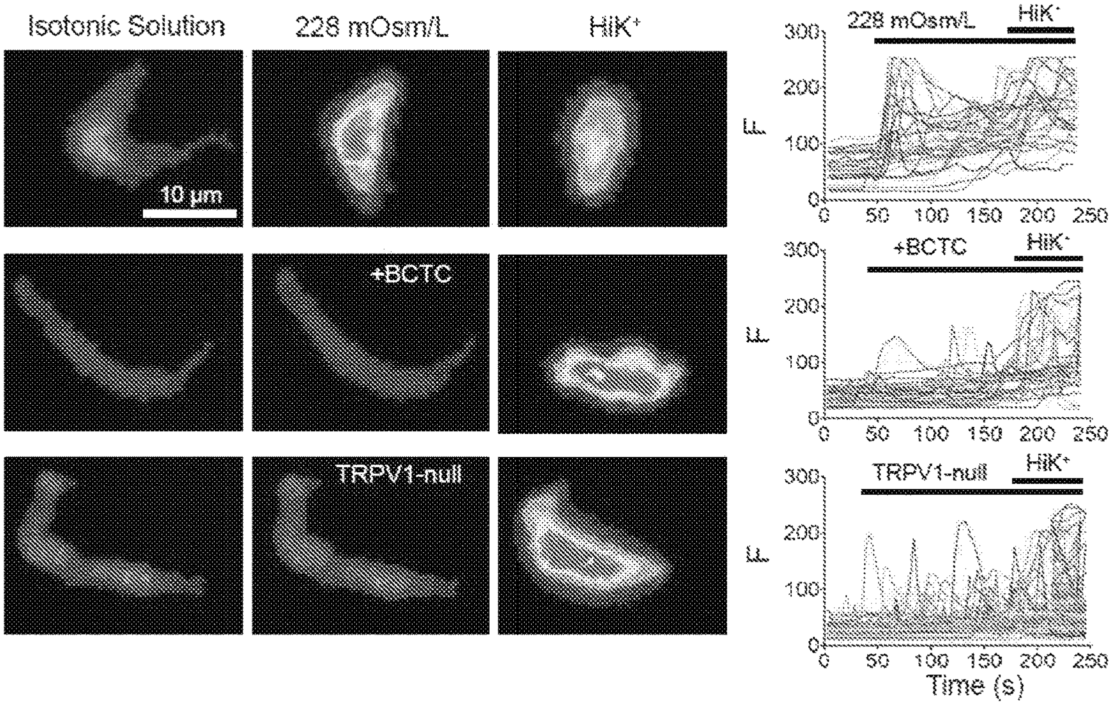
Figure 6B:
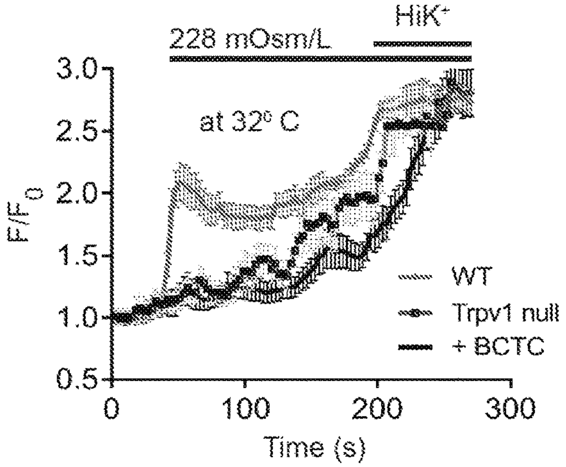
Figure 6C:
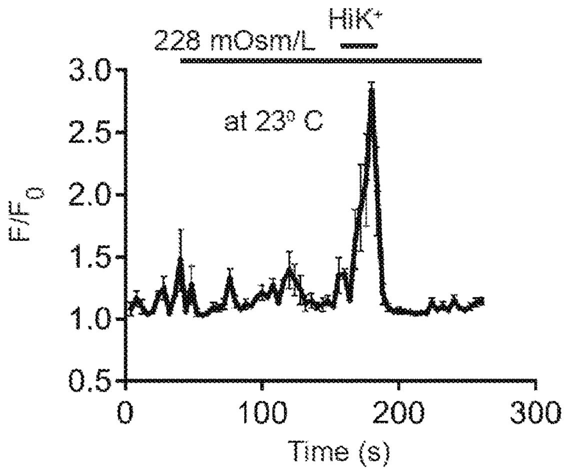
Figure 6D:
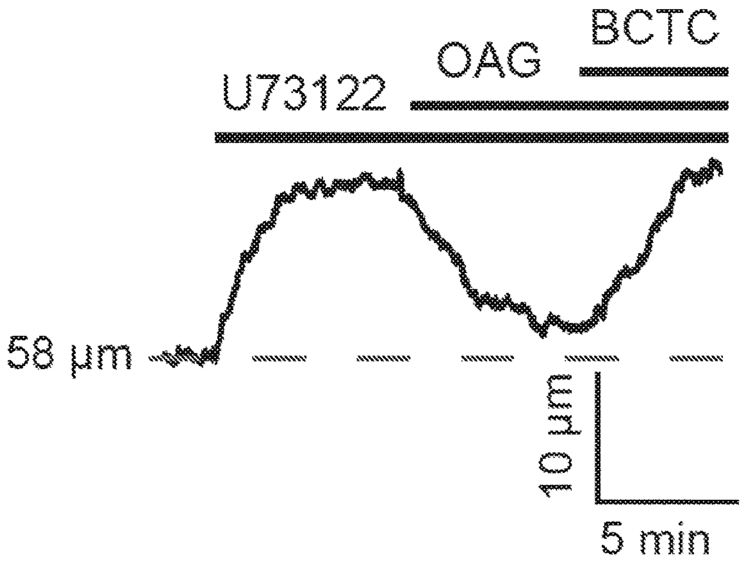
Figure 6E:
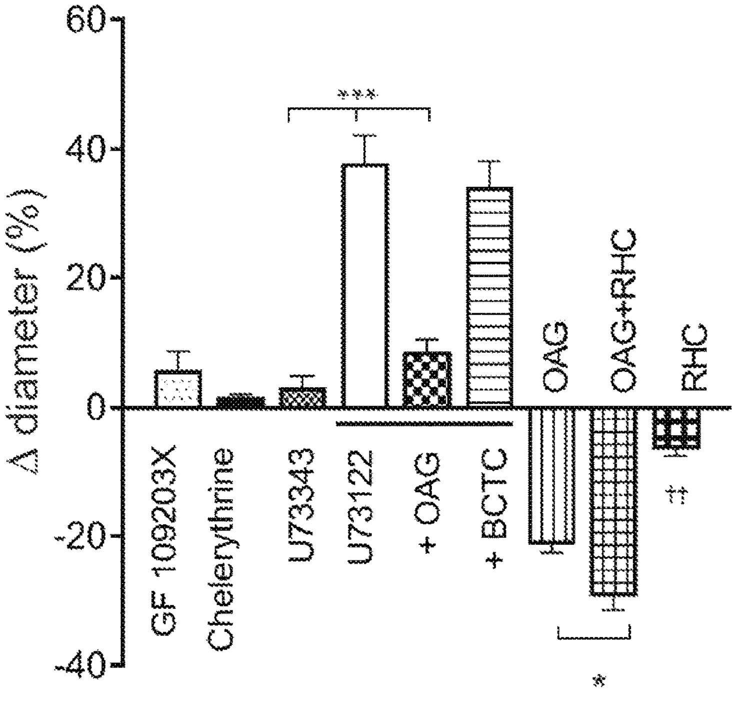
Figure 6F:
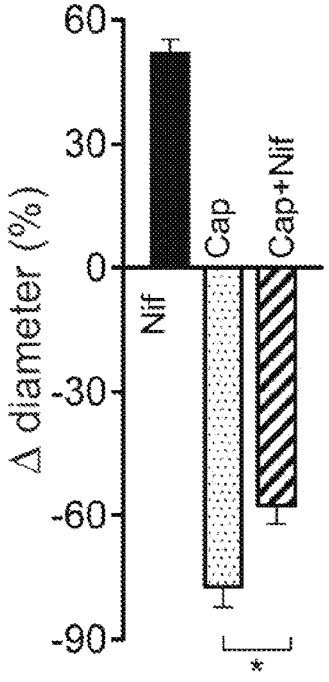
Figure 6G:
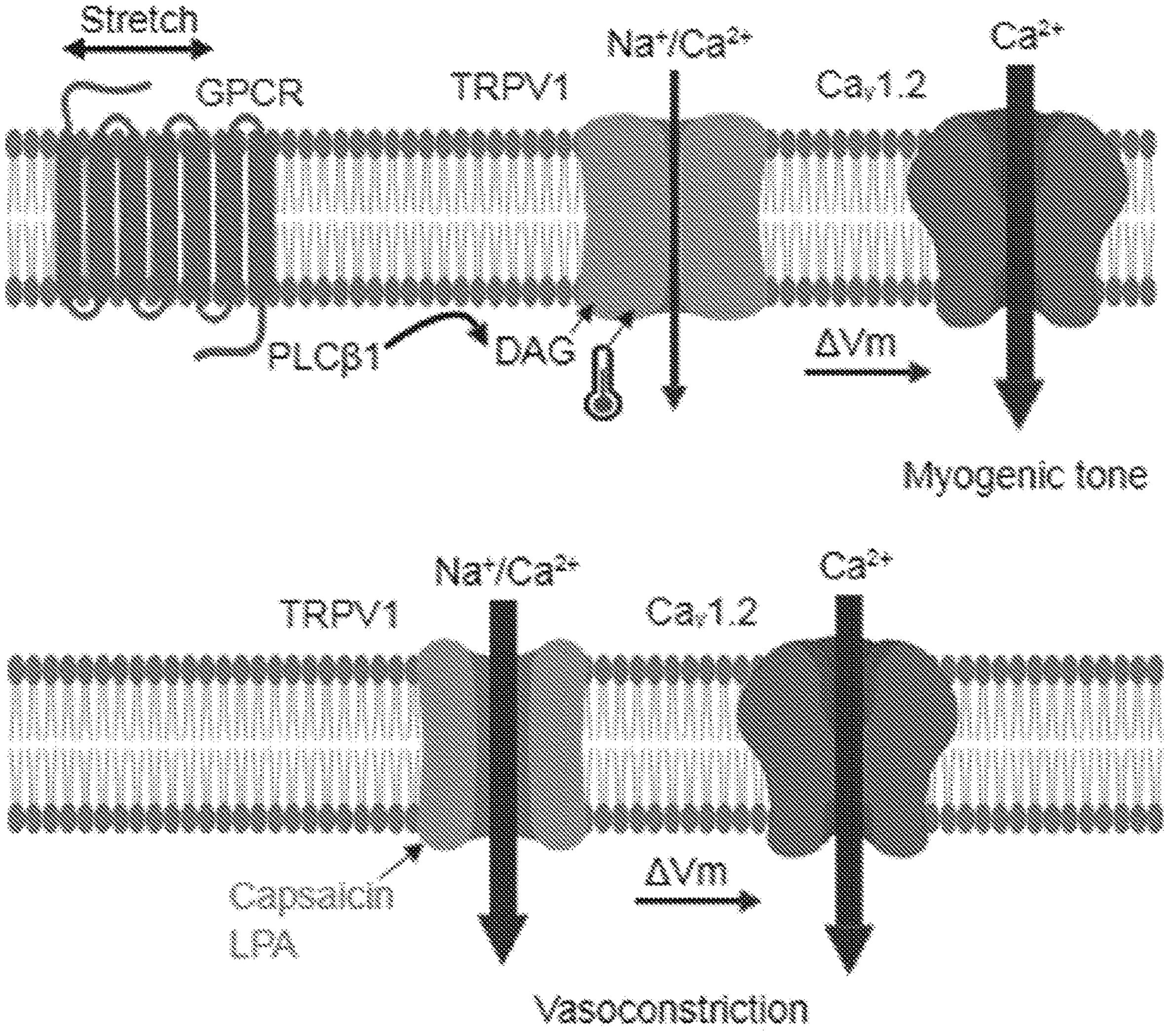
Figure 7A:
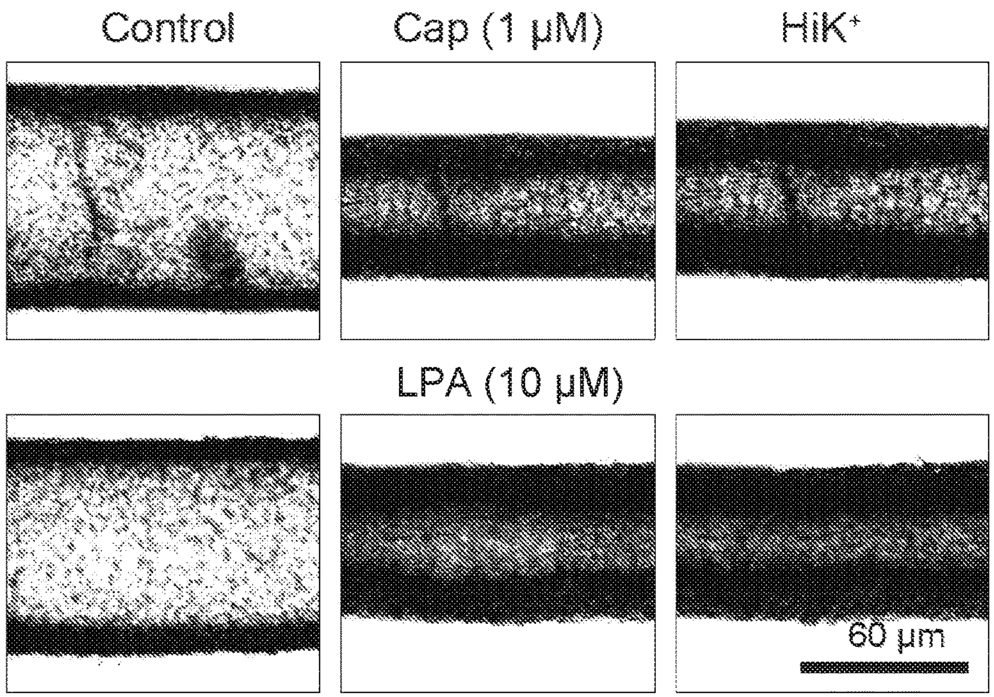
Figure 7B:
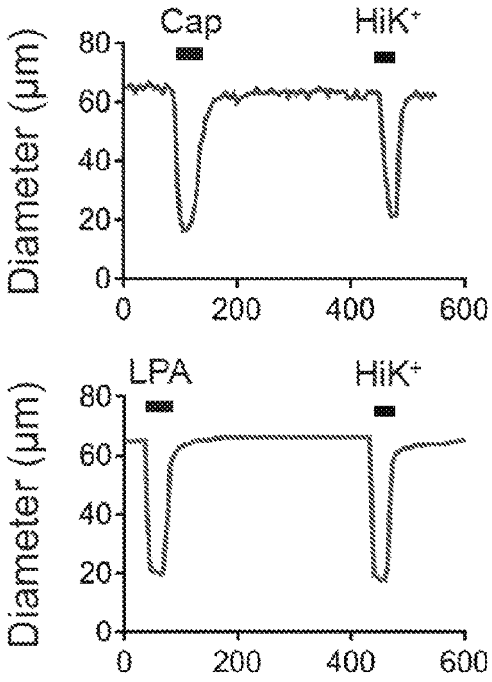
Figure 7C:
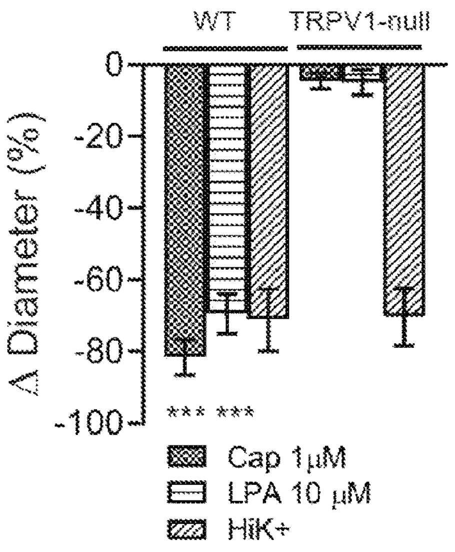
Figure 8:
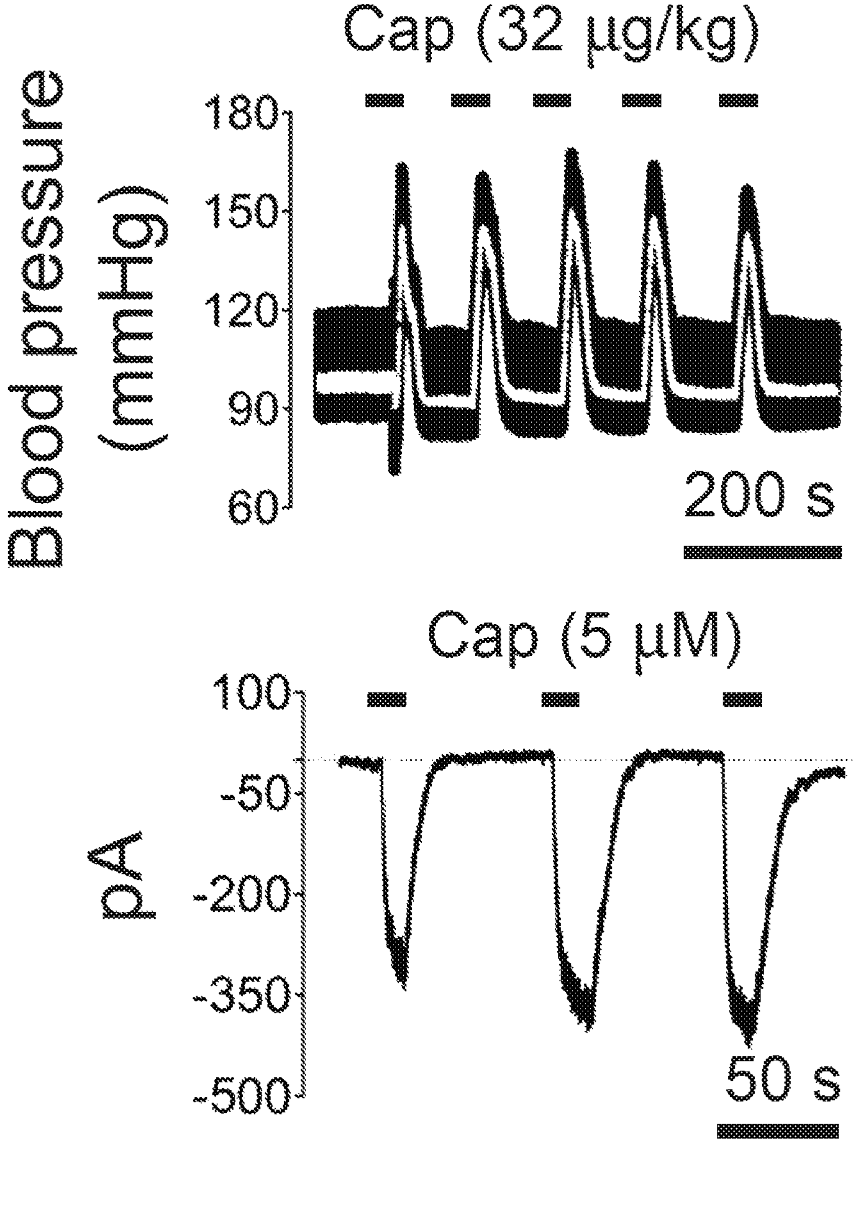
Figure 9:
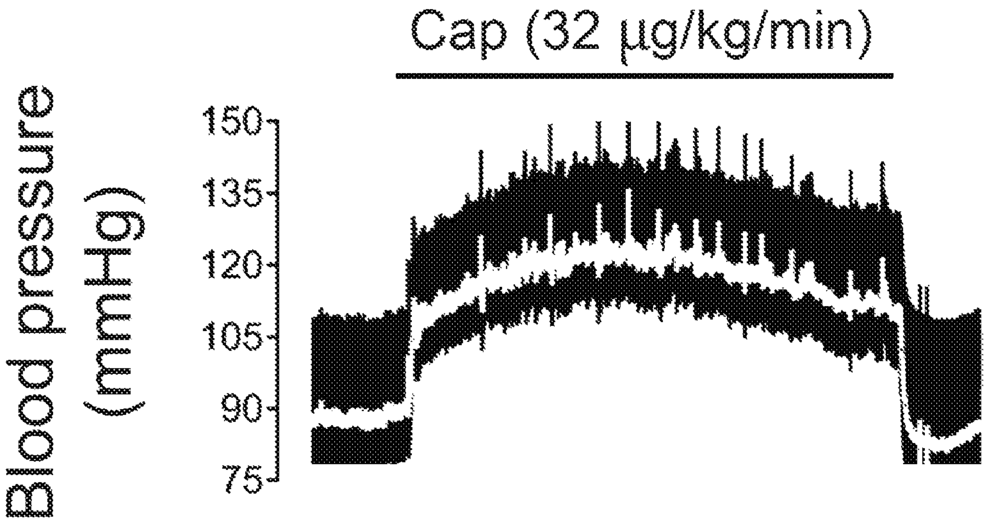
Figure 10:
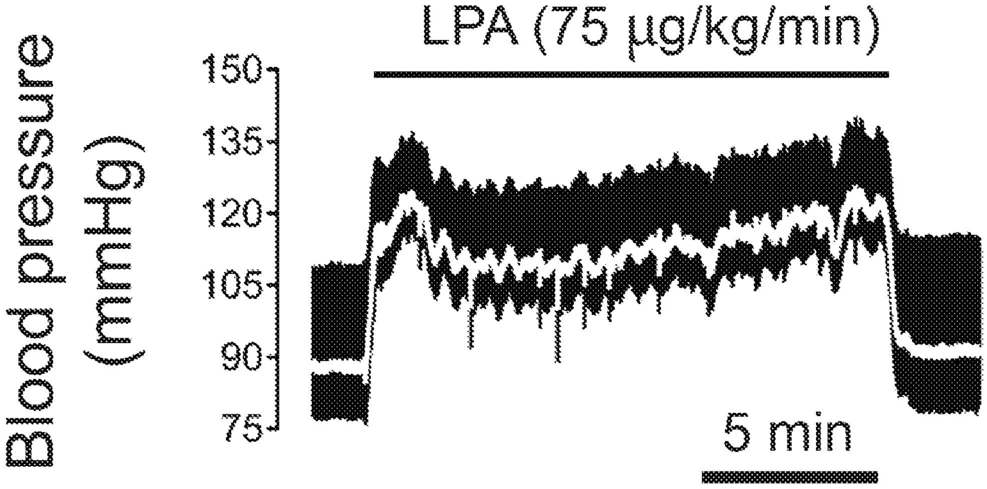
Figure 11:
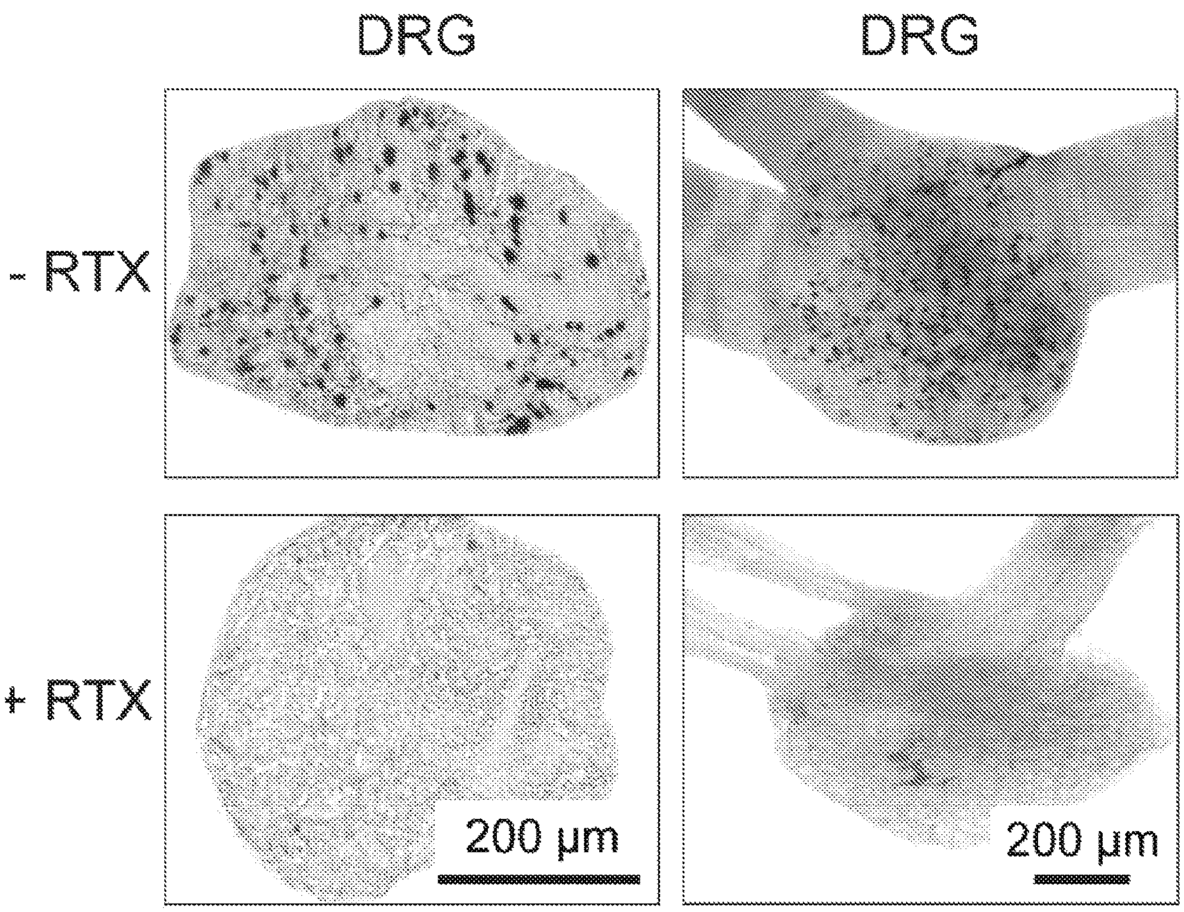

FIG. 4D is a set of graphs which presents data showing that TRPV1 regulates systemic blood pressure, demonstrating mean changes in systolic (SBP) and diastolic (DBP) blood pressure, and heart rate (at peak pressor/depressor response) evoked by capsaicin and BCTC in rats after atropine treatment. (n=6, P<0.01, *P<0.001);

FIG. 4E is a set of graphs which presents data showing that TRPV1 regulates systemic blood pressure, demonstrating mean changes in systolic (SBP) and diastolic (DBP) blood pressure, and heart rate (at peak pressor/depressor response) evoked by capsaicin and BCTC in rats after atropine treatment. (n=6, P<0.01, *P<0.001);

FIG. 4F is a set of graphs which presents data showing that TRPV1 regulates systemic blood pressure, demonstrating blood pressure changes and heart rate in wild-type and TRPV1-null mice in response to IV infusion (20 or 60 s) of capsaicin, lysophosphatidic acid, BCTC, and sodium nitroprusside (n=3-4, P<0.01, *P<0.001) as indicated in the figures;

FIG. 4G is a set of graphs which presents data showing that TRPV1 regulates systemic blood pressure, demonstrating blood pressure changes and heart rate in wild-type and TRPV1-null mice in response to IV infusion (20 or 60 s) of capsaicin, lysophosphatidic acid, BCTC, and sodium nitroprusside (n=3-4, P<0.01, *P<0.001) as indicated in the figures;

FIG. 4H is a set of graphs which presents data showing that TRPV1 regulates systemic blood pressure, demonstrating blood pressure changes and heart rate in wild-type and TRPV1-null mice in response to IV infusion (20 or 60 s) of capsaicin, lysophosphatidic acid, BCTC, and sodium nitroprusside (n=3-4, P<0.01, *P<0.001) as indicated in the figures;

FIG. 4I is a set of graphs which presents data showing that TRPV1 regulates systemic blood pressure, demonstrating blood pressure changes and heart rate in wild-type and TRPV1-null mice in response to IV infusion (20 or 60 s) of capsaicin, lysophosphatidic acid, BCTC, and sodium nitroprusside (n=3-4, P<0.01, *P<0.001) as indicated in the figures;

FIG. 5A is a graph which presents data demonstrating that TRPV1 mediates rapid hyperemia and showing hyperemia following 40 s constriction evoked by KCl or blue light (TRPV1-ChR2 mice) and the reemergence of tone. BCTC and disruption of the TRPV1 gene inhibits the magnitude of the hyperemia and rate of recovery of tone (n=6-10 arteries from 3-6 mice per group, ***P<0.001);

FIG. 5B is a graph which presents data demonstrating that TRPV1 mediates rapid hyperemia and showing hyperemia following 40 s constriction evoked by KCl or blue light (TRPV1-ChR2 mice) and the reemergence of tone. BCTC and disruption of the TRPV1 gene inhibits the magnitude of the hyperemia and rate of recovery of tone (n=6-10 arteries from 3-6 mice per group, ***P<0.001);

FIG. 5C is a graph which presents data demonstrating that TRPV1 mediates rapid hyperemia and showing hyperemia following 40 s constriction evoked by KCl or blue light (TRPV1-ChR2 mice) and the reemergence of tone. BCTC and disruption of the TRPV1 gene inhibits the magnitude of the hyperemia and rate of recovery of tone (n=6-10 arteries from 3-6 mice per group, ***P<0.001);

FIG. 5D is a graph which presents data demonstrating that TRPV1 mediates rapid hyperemia and showing hyperemia in small-diameter (~20 μm) and medium-diameter (~60 μm) arterioles in response to 4 s light (TRPV1-ChR2 mice) or 6 s application of KCl (n=3-5 arteries from 3 mice per group, P<0.01, *P<0.001). FIG. 5H and FIG. 5I show recovery of tone from a maximal dilation (0 $Ca^{2+}$/EGTA) in WT and TRPV1-null mice (n=3 arteries from 3 mice per group, ***P<0.001);

FIG. 5E is a graph which presents data demonstrating that TRPV1 mediates rapid hyperemia and showing hyperemia in small-diameter (~20 μm) and medium-diameter (~60 μm) arterioles in response to 4 s light (TRPV1-ChR2 mice) or 6 s application of KCl (n=3-5 arteries from 3 mice per group, P<0.01, *P<0.001). FIG. 5H and FIG. 5I show recovery of tone from a maximal dilation (0 $Ca^{2+}$/EGTA) in WT and TRPV1-null mice (n=3 arteries from 3 mice per group, ***P<0.001);

FIG. 5F is a graph which resents data demonstrating that TRPV1 mediates rapid hyperemia and showing hyperemia in small-diameter (~20 μm) and medium-diameter (~60 μm) arterioles in response to 4 s light (TRPV1-ChR2 mice) or 6 s application of KCl (n=3-5 arteries from 3 mice per group, P<0.01, *P<0.001). FIG. 5H and FIG. 5I show recovery of tone from a maximal dilation (0 $Ca^{2+}$/EGTA) in WT and TRPV1-null mice (n=3 arteries from 3 mice per group, ***P<0.001);

FIG. 5G is a graph which presents data demonstrating that TRPV1 mediates rapid hyperemia and showing hyperemia in small-diameter (~20 μm) and medium-diameter (~60 μm) arterioles in response to 4 s light (TRPV1-ChR2 mice) or 6 s application of KCl (n=3-5 arteries from 3 mice per group, P<0.01, *P<0.001). FIG. 5H and FIG. 5I show recovery of tone from a maximal dilation (0 $Ca^{2+}$/EGTA) in WT and TRPV1-null mice (n=3 arteries from 3 mice per group, ***P<0.001);

FIG. 5H is a graph which presents data demonstrating that TRPV1 mediates rapid hyperemia and showing hyperemia in small-diameter (~20 μm) and medium-diameter (~60 μm) arterioles in response to 4 s light (TRPV1-ChR2 mice) or 6 s application of KCl (n=3-5 arteries from 3 mice per group, P<0.01, *P<0.001). FIG. 5H and FIG. 5I show recovery of tone from a maximal dilation (0 $Ca^{2+}$/EGTA) in WT and TRPV1-null mice (n=3 arteries from 3 mice per group, ***P<0.001);

FIG. 5I is a graph which presents data demonstrating that TRPV1 mediates rapid hyperemia and showing hyperemia in small-diameter (~20 μm) and medium-diameter (~60 μm) arterioles in response to 4 s light (TRPV1-ChR2 mice) or 6 s application of KCl (n=3-5 arteries from 3 mice per group, P<0.01, *P<0.001). FIG. 5H and FIG. 5I show recovery of tone from a maximal dilation (0 $Ca^{2+}$/EGTA) in WT and TRPV1-null mice (n=3 arteries from 3 mice per group, ***P<0.001);

FIG. 6A is a set of images and graphs which demonstrate that stretch of arterial smooth muscle cells activates TRPV1 in a PLC and heat dependent manner and shows $Ca^{2+}$ signaling evoked by a hypo-osmotic solution in ASM cells isolated from wild-type and TRPV1-null mice. Both BCTC (1 μM) and reducing temperature from 32° C. to 23° C. inhibits the stretch-evoked response (n=30-50 cells per group from 3 independent experiments);

FIG. 6B is a graph which demonstrates that stretch of arterial smooth muscle cells activates TRPV1 in a PLC and heat dependent manner and shows $Ca^{2+}$ signaling evoked by a hypo-osmotic solution in ASM cells isolated from wild-type and TRPV1-null mice. Both BCTC (1 μM) and reducing temperature from 32° C. to 23° C. inhibits the stretch-evoked response (n=30-50 cells per group from 3 independent experiments);

FIG. 6C is a graph which demonstrates that stretch of arterial smooth muscle cells activates TRPV1 in a PLC and heat dependent manner and shows $Ca^{2+}$ signaling evoked by a hypo-osmotic solution in ASM cells isolated from wild-type and TRPV1-null mice. Both BCTC (1 μM) and reducing temperature from 32° C. to 23° C. inhibits the stretch-evoked response (n=30-50 cells per group from 3 independent experiments);

FIG. 6D is a graph which demonstrates that stretch of arterial smooth muscle cells activates TRPV1 in a PLC and heat dependent manner and shows in vivo changes in arterial diameter during treatment with PLC inhibitor, U73122 (10 μM) and the inactive analog U73343 (10 μM); PKC inhibitors, GF 109203X and chelerythrine chloride (10 μM); diacylglycerol analog, 1-Oleoyl-2-acetyl-sn-glycerol (OAG, 50 μM); RHC80267 (10 μM), (n≥5 arteries from 3 mice per group, *P<0.05, ***P<0.001, ff P<0.05 paired t-test);

FIG. 6E is a graph which demonstrates that stretch of arterial smooth muscle cells activates TRPV1 in a PLC and heat dependent manner and shows in vivo changes in arterial diameter during treatment with PLC inhibitor, U73122 (10 μM) and the inactive analog U73343 (10 μM); PKC inhibitors, GF 109203X and chelerythrine chloride (10 μM); diacylglycerol analog, 1-Oleoyl-2-acetyl-sn-glycerol (OAG, 50 μM); RHC80267 (10 μM), (n≥5 arteries from 3 mice per group, *P<0.05, ***P<0.001, ff P<0.05 paired t-test);

FIG. 6F is a graph which demonstrates that stretch of arterial smooth muscle cells activates TRPV1 in a PLC and heat dependent manner and shows arterial diameter following treatment with nifidepine, capsaicin, and nifedipine/capsaicin, n=3-5, *P<0.05;

FIG. 6G is a diagram which demonstrates that stretch of arterial smooth muscle cells activates TRPV1 in a PLC and heat dependent manner and shows a proposed signaling cascade for the generation of myogenic tone. Mediators indicated as underlined were confirmed while bolded italic mediators were excluded by pharmacologic or genetic interventions;

FIG. 7A is a set if images which shows the effects of application of capsaicin and LPA (C18:1) to a pressurized radial branch artery from a WT mouse, providing further evidence of the effects of TPRV1 agonists on causing constriction of pressurized arteries;

FIG. 7B is a set of graphs which shows the data of FIG. 7A. FIG. 7C summarizes the data for WT and TRPV1-null mice (n=5-6), providing further evidence of the effects of TPRV1 agonists on causing constriction of pressurized arteries;

FIG. 7C is a graph which summarizes the data for WT and TRPV1-null mice (n=5-6), providing further evidence of the effects of TPRV1 agonists on causing constriction of pressurized arteries;

FIG. 8 is a set of graphs which shows data demonstrating that the capsaicin-evoked pressor effect does not exhibit tachyphylaxis. Repeated injections of capsaicin produce similar increases in BP. Nondesensitizing currents are provided in a voltage-clamped vascular smooth muscle cell;

FIG. 9 is a graph which shows data demonstrating that capsaicin infusion produced a sustained increase in BP;

FIG. 10 is a graph which shows data demonstrating that LPA infusion also produced a sustained increase in BP; and FIG. 11 is a set of images which shows images demonstrating nLacZ staining in DRG from TRPV1-nLacZ reporter mice with and without systemic RTX treatment.

SUMMARY OF THE INVENTION

Provided herein are methods of treatment of hypotension in a human patient in septic shock, the method comprising administering at least one TRPV1 agonist to the patient in an amount sufficient to increase and maintain systolic blood pressure to greater than 65 mm Hg. In certain embodiments, the TRPV1 agonist is selected from one or more of a capsaicin, daphnane TRPV1 agonists, vanillotoxin, N-oleoyl dopamine, N-arachidonyl dopamine, BrP-LPA, and derivatives and analogues thereof.

In certain embodiments, the capsaicin analogue is selected from oleoylvanillamine, rinvanil and phenylacetylrinvanil.

In certain embodiments, the vanillotoxin is DkTx or a derivative or analogue thereof.

In certain embodiments the daphnane TRPV1 agonist is selected from resinaferotoxin and tinyatoxin.

In certain embodiments, the TRPV1 agonist is co-administered with an adrenergic agonist selected from dopamine, phenylephrine, norepinephrine, and metaraminol.

In other embodiments, the TRPV1 agonist is co-administered with an angiotensin. In certain embodiments the angiotensin is selected from Angiotensin II, Angiotensin III and Angiotensin IV.

The TRPV1 agonist may be administered intravenously in some embodiments, while in other embodiments the TRPV1 agonist is administered by topical patch.

Also provided are pharmaceutical formulations for increasing blood pressure in septic shock, the formulations including at least one TRPV1 agonist in a dosage form for parenteral administration, wherein the TRPV1 agonist is selected from capsaicin, daphnane TRPV1 agonists, vanillotoxin, N-oleoyl dopamine, N-arachidonyl dopamine, BrP-LPA, and derivatives and analogues thereof. The formulation is lyophilized for reconstitution in certain embodiments. In certain embodiments, the pharmaceutical formulation including at least one TRPV1 agonist in a dosage form for parenteral administration further comprises a co-lyophilized adrenergic agonist selected from dopamine, phenylephrine, norepinephrine, and metaraminol. In other embodiments, pharmaceutical formulations including at least one TRPV1 agonist in a dosage form for parenteral administration is contemplated, where the formulation is co-lyophilized with an angiotensin selected from Angiotensin II, Angiotensin III, and Angiotensin IV.

DETAILED DESCRIPTION OF THE PREFERRED EMBODIMENTS

In describing preferred embodiments of the invention illustrated in the drawings, specific terminology will be resorted to for the sake of clarity. However, the invention is not intended to be limited to the specific terms so selected, and it is to be understood that each specific term includes all technical equivalents that operate in a similar manner to accomplish a similar purpose. Several preferred embodiments of the invention are described for illustrative purposes, it being understood that the invention may be embodied in other forms not specifically shown in the figures.

Provided herein are systems and methods of stabilizing blood pressure in severe sepsis/septic shock and other types of distributive shock using TRPV1 agonists. Notably, because TRPV1 is not expressed in the arterial blood supply of the spleen/kidney/liver, TRPV1-mediated vasoconstriction can safely maintain BP while preserving blood flow to these critical organs.

Arteries must deliver blood to tissues within a narrow pressure range to enable adequate perfusion without damaging capillaries. These vessels possess the intrinsic capacity to sense changes in local blood pressure and promptly adjust their caliber in order to stabilize blood flow. However, the underlying mechanisms for this autoregulatory phenomenon have not been well understood. As provided herein, the TRPV1 ion channel is shown to have an essential role for in arterial smooth muscle mechanotransduction and the regulation of blood flow in various tissues. As herein provided, reporter mice and functional studies show that TRPV1 channels tile the arterial smooth muscle in the microcirculation of skeletal muscle, heart, fat, and brain. Activation of TRPV1 pharmacologically, or TRPV1-positive cells optogenetically, constricts arteries and increases systemic blood pressure. In contrast, TRPV1 antagonists dilate arteries and decrease blood pressure. Membrane stretch indirectly activates TRPV1 via a temperature-dependent mechanism involving phospholipase C and diacylglycerol signaling. Conversely, arteriole occlusion leading to reduced membrane tension, deactivates TRPV1 to rapidly dilate arterioles. Further, lysophosphatidic acid, a bioactive lipid generated by platelets and atherogenic plaques, markedly increases systemic blood pressure via TRPV1. Thus, we show that TRPV1 serves as a critical transduction channel for myogenic tone and confers both dynamic regulation of blood flow and sensitivity to inflammatory vasoconstrictors. This finding forms a basis for a treatment of septic shock provided herein.

While the making and using of various embodiments of the present invention are discussed in detail below, it should be appreciated that the present invention provides many applicable inventive concepts which can be employed in a wide variety of specific contexts. The specific embodiments discussed herein are merely illustrative of specific ways to make and use the invention and do not delimit the scope of the invention.

To facilitate the understanding of this invention, and for the avoidance of doubt in construing the claims herein, a number of terms are defined below. Terms defined herein have meanings as commonly understood by a person of ordinary skill in the areas relevant to the present invention. The terminology used to describe specific embodiments of the invention does not delimit the invention, except as outlined in the claims.

The terms such as "a," "an," and "the" are not intended to refer to a singular entity unless explicitly so defined, but include the general class of which a specific example may be used for illustration. The use of the terms "a" or "an" when used in conjunction with "comprising" in the claims and/or the specification may mean "one" but may also be consistent with "one or more," "at least one," and/or "one or more than one."

The use of the term "or" in the claims is used to mean "and/or" unless explicitly indicated to refer to alternatives as mutually exclusive. Thus, unless otherwise stated, the term "or" in a group of alternatives means "any one or combination of" the members of the group. Further, unless explicitly indicated to refer to alternatives as mutually exclusive, the phrase "A, B, and/or C" means embodiments having element A alone, element B alone, element C alone, or any combination of A, B, and C taken together.

Similarly, for the avoidance of doubt and unless otherwise explicitly indicated to refer to alternatives as mutually exclusive, the phrase "at least one of" when combined with a list of items, means a single item from the list or any combination of items in the list. For example, and unless otherwise defined, the phrase "at least one of A, B and C," means "at least one from the group A, B, C, or any combination of A, B and C." Thus, unless otherwise defined, the phrase requires one or more, and not necessarily not all, of the listed items.

The terms "comprising" (and any form thereof such as "comprise" and "comprises"), "having" (and any form thereof such as "have" and "has"), "including" (and any form thereof such as "includes" and "include") or "containing" (and any form thereof such as "contains" and "contain") are inclusive or open-ended and do not exclude additional, unrecited elements or method steps.

The term "effective" as used in the specification and claims, means adequate to provide or accomplish a desired, expected, or intended result.

The terms "about" or "approximately" are defined as being close to as understood by one of ordinary skill in the art, and in one non-limiting embodiment the terms are defined to be within 10%, within 5%, within 1%, and in certain aspects within 0.5%.

For purposes of this specification and the claims appended thereto, the term "sepsis" means a life-threatening organ dysfunction caused by a dysregulated host response to infection. The term "septic shock" is used herein refers to a subset of sepsis in which underlying circulatory and cellular/metabolic abnormalities are profound enough to substantially increase mortality. Clinically, septic shock involves a finding of sepsis together with hypotension (generally a systolic blood pressure of less than 65 mm Hg) and an elevated lactate level (lactate>2 mmol/L (18 mg/dL) despite adequate fluid resuscitation), which is indicative of one or more of insufficient tissue oxygen delivery, impaired aerobic respiration, accelerated aerobic glycolysis, and reduced hepatic clearance.

ABBREVIATIONS: The following abbreviations are used throughout this application:

BCTC N-(4-Tertiarybutylphenyl)-4-(3-cholorphyridin-2-yl)tetrahydropyrazine-1(2H)-carbox-amide
BrP-LPA [(3S)-1-bromo-4-hexadecanoyloxy-3-hydroxy-butyl]phosphonic acid
Capsaicin 8-methyl-N-vanillyl-trans-6-nonenamide
DAGL Diacylglycerol lipase
DkTx tarantula double-knot toxin
GPCRS G protein-coupled receptors (GPCRs), aka seven (pass)-transmembrane domain receptors, 7™ receptors, heptahelical receptors, serpentine receptor, and G protein-linked receptors (GPLR)
LPA lysophosphatidic acid
LPS lipopolysaccaride
nLacZ nuclear R galactosidase
OAG 1-Oleoyl-2-acetyl-sn-glycerol
PLAP human placental alkaline phosphatase
PLC Phospholipase C
RTX resiniferatoxin
TRPC Transient Receptor Potential (TRP) channels
TRPV1 Transient receptor potential vanilloid 1 cation channel For over a century it has been known that vascular myogenic tone includes constriction of arterioles in the face of increased intravascular pressure and dilation in response to decreased intravascular pressure. This autoregulatory property maintains tissue perfusion despite fluctuations in blood pressure and contributes to reactive hyperemia, the increase in blood flow following a brief interruption in supply. Although an intrinsic property of vascular smooth muscle, myogenic tone is not uniformly distributed along the arterial tree, being enriched in terminal arterioles and practically non-existent in large conduit arteries (>150 μm diameter). The presence of myogenic tone in small arteries and arterioles, counteracted by metabolic factors, allows for discrete, local control of blood flow in organs such as the heart, brain and skeletal muscle. Despite the physiological importance of myogenic tone, details of the underlying molecular machinery are only just emerging. See Hill, MA & Meininger, GA. "Arteriolar vascular smooth muscle cells: mechanotransducers in a complex environment" *Int. J Biochem & Cell Biol.* 44 (2012) 1505-1510. Although smooth muscle cells within the arteriolar wall express mechanosensitive ion channels such as Piezol, these do not appear to contribute to normal myogenic tone. Rather, several studies support a role for Gq/11 G-protein coupled receptors (GPCRs) as mechanosensors in vascular smooth muscle. In turn, GPCR-mediated phospholipase (PLC) signaling activates transduction channels that depolarize the plasma membrane to trigger voltage-gated Ca2+ entry and ultimately smooth muscle contraction. The identity of the transduction channels is unclear but Transient Receptor Potential (TRP) channels are candidates. TRPC6 and TRPM4 channels are implicated in the tone of cerebral and mesenteric arterioles, although myogenic tone is retained in mice deficient in TRPC6 and TRPM4 suggesting the existence of alternative mechanisms. Indeed, the heterogeneous properties of arteries in different vascular beds supports different underlying mechanisms for myogenic tone. Another ion channel expressed in vascular smooth muscle cells is TRPV1, best known as a sensory nerve detector of noxious stimuli, including capsaicin, endogenous bioactive lipids, extracellular protons and heat. However, there has heretofore been limited information on the distribution and physiological function of TRPV1 in arteries. Here we show that TRPV1 specifically localizes to small arterioles in numerous tissues. Further, functional analyses provided herein show that TRPV1 controls rapid myogenic tone and systemic blood pressure revealing a generalized mechanism for blood flow regulation.

The data provided here reveal a critical role for TRPV1 in the rapid control of myogenic tone and provide a novel method in the treatment of circulatory collapse that is critical in the control and reversal of septic shock. TRPV1 is known to localize to small diameter arteries of tissues with high spontaneous myogenic tone including the heart, skeletal muscle, brain sub regions and fat, but is absent in tissues with little to no myogenic tone, such as lung, liver and gut. Thus, TRPV1 could be considered to provide a generalized mechanism for the autoregulation of blood flow. However, there are exceptions as found here. It was found that there is limited expression of TRPV1 in kidney and forebrain, both of which possess prominent myogenic tone, suggesting the existence of distinct auto regulatory mechanisms in these vascular beds.

In considering the biophysical properties of TRPV1 that enable rapid control of vessel diameter, it is known that allosteric coupling of distinct ligand, voltage, and temperature sensors drive the gating of TRPV1 and other thermo- TRP channels. In that way, combined sub-threshold stimuli can effectively open the channel.

It has been found that changes in levels of DAG generated by membrane stretch, combined with heat stimuli, confer fast activation and deactivation of TRPV1 and myogenic tone. Notably, while it was known that whereas DAG analogs fail to activate TRPV1 at room temperature they are effective agonists at 37° C., albeit with a low potency (EC50 of 42 μM). See Hofmann, T. et al. "Direct activation of human TRPC6 and TRPC3 channels by diacylglycerol" Nature 397 (1999) 259-263; Woo, D. H. et al. "Direct activation of transient receptor potential vanilloid 1 (TRPV1) by diacylglycerol (DAG)" Molecular Pain 4 (2008) 42. Thus, it can be concluded that DAG has a low intrinsic efficacy and potency at TRPV1 but can activate the channel in concert with heat. The low affinity of DAG, however, would facilitate fast deactivation of TRPV1 and consequently a rapid decrease in myogenic tone when transmural pressure falls, thus generating a rapid reactive hyperemia.

In sensory nerves, diverse inflammatory mediators activate or sensitize TRPV1 to exacerbate pain. The data provided herein show that these stimuli act on arterial TRPV1 to mediate vasoconstriction, corroborated by the finding that LPA increases systemic blood pressure via TRPV1. Indeed, TRPV1 in coronary arteries represents a prime target for LPA generated by atherogenic plaques. Furthermore, in experimental sepsis TRPV1-null mice exhibit both a greater fall in blood pressure and a higher mortality than their wild-type counterparts, suggesting that TRPV1-mediated vasoconstriction contributes to hemostasis. These observations indicate important roles for TRPV1 in regulating vasoconstriction and blood pressure in disease and injury states.

In certain embodiment provided herein, TRPV1 agonists are employed for treatment of hypotension in septic shock. Vanilloids, such as capsaicinoids, are examples of TRPV1 agonists. Exemplary vanilloids for use according to the invention include N-vanillyl-alkanedienamides, N-vanillyl-alkanedienyls, N-vanillyl-cis-monounsaturated alkenamides, capsaicin, dihydrocapsaicin, norhydrocapsaicin, nordihydrocapsaicin, homocapsaicin, and homodihydrocapsaicin.

In one embodiment, capsaicin, capsaicin analogues and derivatives thereof that agonize TRPV1 is administered to raise systolic blood pressure over 65 mm Hg. Capsaicin, 8-methyl-N-vanillyl-6-nonenamide, has the chemical structure:

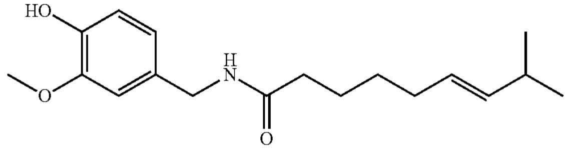 [SMILES: COc1cc(CNC(=O)CCCC/C=C/C(C)C)ccc1O]

In certain embodiments, an injectable form of capsaicin is employed in the stabilization of blood pressure in septic shock. One such long acting, ultra-pure injectable synthetic form of capsaicin is ADLEA™ (Algrx-4975), developed by Anesiva Inc. In another embodiment the capsaicin derivative is a synthetic trans-capsaicin referred to as Qutenza® (NGX-4010) in a high concentration rapid-delivery patch by NeurogesX, Inc.

In certain embodiments, an injectable form of a capsaicin analogue selected from one or more of oleoylvanillamine, rinvanil and phenylacetylrinvanil is employed in the stabilization of blood pressure in septic shock. The capsaicin analogue oleoylvanillamine (a.k.a. N-vanillyloleamide, N-vannilyloleoylamide, and Olvanil) has the following structure:

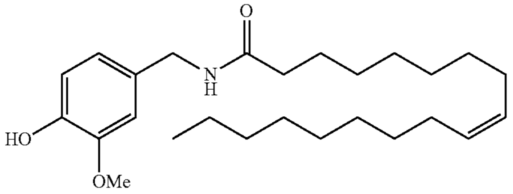 [SMILES: CCCCCCCC/C=C\CCCCCCCC(=O)NCc1ccc(O)c(OC)c1]

The capsaicin analogue rinvanil has the following structure:

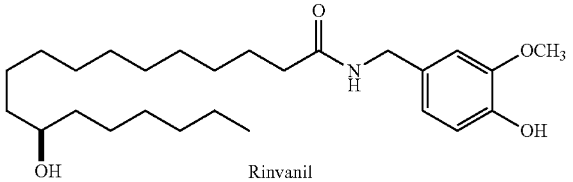 [SMILES: CCCCCC[C@@H](O)CCCCCCCCCCC(=O)NCc1ccc(O)c(OC)c1]

Rinvanil

The capsaicin analogue phenylacetylrinvanil has the following structure:

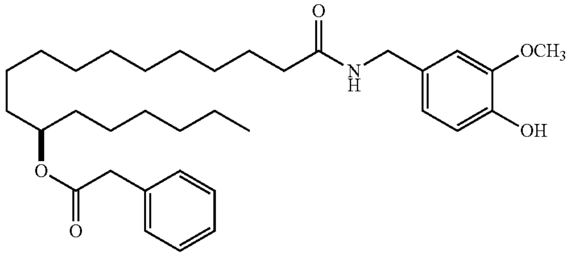 [SMILES: CCCCCC[C@H](CCCCCCCCCCC(=O)NCc1ccc(O)c(OC)c1)OC(=O)Cc1ccccc1]

In another embodiment, the TRPV1 agonist is an α-bromophosphonate such as BrP-LPA and analogues and derivatives thereof that act as TRPV1 agonists. BrP-LPA ([(3S)-1-bromo-4-hexadecanoyloxy-3-hydroxybutyl]phosphonic acid, CAS No: 944265-88-7) has the following structure:

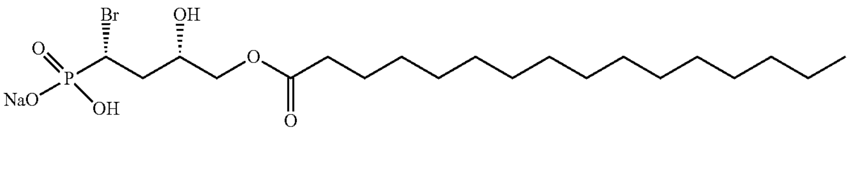

BrP-LPA activates TRPV1 with little to no desensitization to achieve a more sustained pressor effect. In addition to its pressor action, BrP-LPA has the advantage of being anti-coagulant (by antagonizing LPA receptors), and is expected to satisfy this further requirement in the context of sepsis.

In another embodiment, a vanillotoxin is utilized as a TRPV1 agonist. In one embodiment the vanillotoxins (VaTx) is a spider peptide toxin that activates TRPV1 by interacting with the channel's outer pore region. Three such toxins (VaTx1, VaTx2, and VaTx3) reversibly activate TRPV1, while the fourth vanillotoxin, double-knot toxin (DkTx), has been shown to cause a slowly developing and persistent activation of the TRPV1 channel. See Bohlen C J, et al. "A Bivalent Tarantula Toxin Activates the Capsaicin Receptor TRPV1, by Targeting the Outer Pore Domain" Cell 141(5) (2010) 834-845. DkTx activates TRPV1 with little to no desensitization to achieve a more sustained pressor effect. DkTx is a peptide with an atypical bivalent structure having two ICK peptide lobes (Knot 1 and Knot 2) connected by a linker. DkTx is able to lock TRPV1 in its open state and evoke an irreversible channel activation. The high avidity of DkTx at TRPV1 offers the potential for very selective agonism of TRPV1 with minimal CNS effects.

In other embodiments, the TRPV1 agonist is a daphnane molecule. Daphnanes are tricyclic diterpenes with a tricyclo [9.3.0.0]tetradecane ring system. Examples of daphnane that function as TRPV1 agonists include resiniferatoxin (RTX) and tinyatoxin (TTX or TTN). RTX and TTX occur naturally in the seeds and sap of Euphorbiaceae species of plants. The structure of resiniferatoxin is shown below:

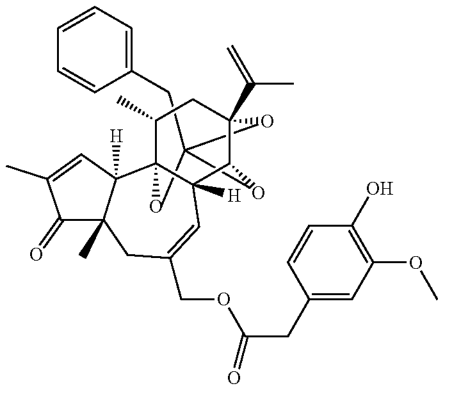

TRPV1 agonists may trigger pain responses due to activation of sensory nerves, thus, in certain embodiments, pain control is effected by an initial slow to very slow infusion rate, which will limit sensory nerve activation (due to desensitization of TRPV1, as would be the case for capsaicin, or alternatively via depolarization block, as would be the case for DkTx).

In certain embodiments, the TRPV1 agonist is a fatty acid dopamine conjugate selected from N-oleoyl dopamine and N-arachidonyl dopamine. N-Arachidonoyl dopamine (CAS No. 199875-69-9) is an endocannabinoid found in the human CNS, which is structurally similar to capsaicin and activates the TRPV1 channel with an $EC_{50}$ of approximately of 50 nM. See Huang S M, et al. "An endogenous capsaicin-like substance with high potency at recombinant and native vanilloid VR1 receptors" *Proc. Natl. Acad. Sci. U.S.A.* 99 (12) (2002) 8400-5. N-Arachidonoyl dopamine has the structure set out below:

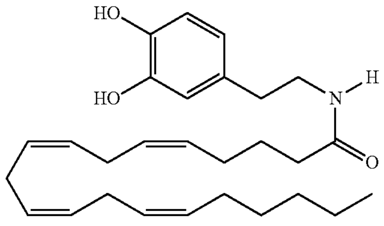 [SMILES: CCCCC/C=C\C/C=C\C/C=C\C/C=C\CCCC(=O)NCCc1ccc(O)c(O)c1]

N-Oleyl-dopamine (CAS No. 105955-11-1) is another endogenous agonist that binds to human vanilloid receptor VR1 with an Ki of 36 Nm, thus making it equipotent to capsaicin. The structure of N-oleyl-dopamine is set out below:

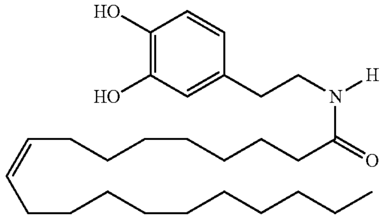 [SMILES: CCCCCCCCCC/C=C\CCCCCCCC(=O)NCCc1ccc(O)c(O)c1]

In certain embodiments, the TRPV1 agonist is co-administered with a vasoconstrictor drug to further increase systemic blood pressure in cardiovascular shock. In certain embodiments, the vasoconstrictor drugs are adrenergic agonists. Adrenergic agonists that act as vasoconstrictors and that are presently used to increase blood pressure include dopamine (3,4-dihydroxyphenethylamine), phenylephrine, norepinephrine (LEVOPHED), and metaraminol (ARAMINE). In certain embodiments, the TRPV1 agonist is co-administered with an adrenergic agonist.

An example of an adrenergic agonist currently employed for stabilization of blood pressure in Angiotensin II. Angiotensin II is a peptide hormone having the sequence Asp-Arg-Val-Tyr-Ile-His-Pro-Phe (SEQ ID NO. 1) that is converted from Angiotensin I by removal of two C-terminal residues by angiotensin-converting enzyme (ACE). In certain embodiments, the TRPV1 agonist is co-administered with an angiotensin. In particular embodiments, the Angiotensin is Angiotensin II. In other embodiments, the TRPV1 agonist is co-administered with Angiotensin III (Arg-Val-Tyr-Ile-His-Pro-Phe; SEQ ID NO. 2) or Angiotensin IV (Val-Tyr-Ile-His-Pro-Phe; SEQ ID NO. 3), which have reduced pressor activity relative to Angiotensin II. Angiotensin II as a peptide hormones is labile and is supplied in lyophilized form for reconstituted with 0.9% Saline (NaCl) immediately prior to injection. The Angiotensin II approved for inducing vasoconstriction is the synthetic Angiotensin II acetate having the chemical name L-Aspartyl-L-arginyl-L-valyl-L-tyrosyl-L-isoleucyl-L-histidyl-L-prolyl-L-phenylalanine, acetate salt. The counter ion acetate is present in a non-stoichiometric ratio. It is a white to off-white powder, soluble in water. The half-life of Angiotensin II after administration is less than one minute and is thus administered by continuous infusion.

In certain embodiments, the TRPV1 agonist is co-lyophilized with at least one adrenergic agonist and is provided in a vial for reconstitution with saline for parental administration. In certain embodiments the TRPV1 agonist is co-lyophilized with at least one angiotension and is provided in a vial for reconstitution with saline for parental administration.

The following examples are included for the sake of completeness of disclosure and to illustrate the methods of making the compositions and composites of the present invention as well as to present certain characteristics of the compositions. In no way are these examples intended to limit the scope or teaching of this disclosure.

Figure 1A:
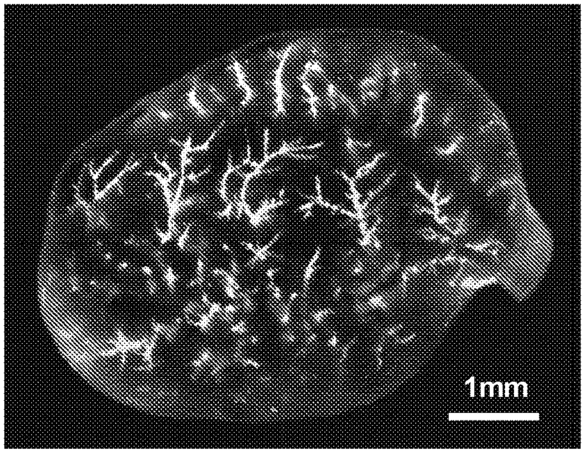
FIG. 1A is an image which show expression of TRPV1 in TRPV1 reporter mice and reveal TRPV1 expression in small arterioles of the ventricular myocardium.
Figure 1B:
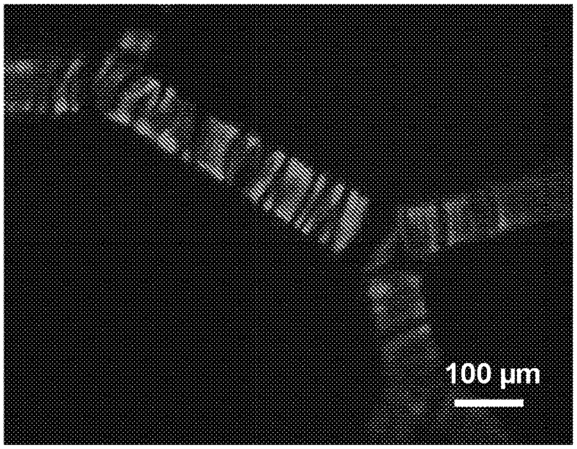
FIG. 1B is an image which shows expression of TRPV1 in TRPV1 reporter mice and reveals TRPV1 expression in small arterioles of the ventricular myocardium where there is an analysis of whole hearts and transverse heart sections from TRPV1-Cre:tdTomato mice.
Figure 1C:
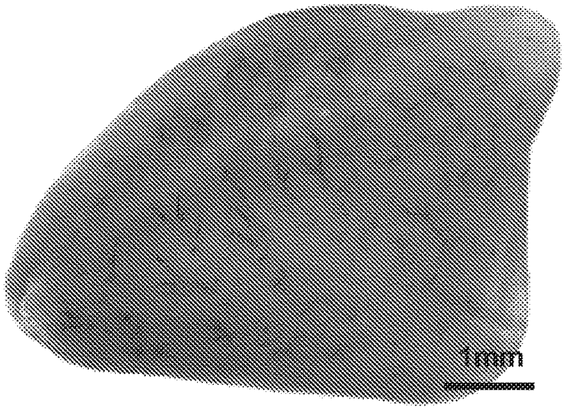
FIG. 1C is an image which shows expression of TRPV1 in TRPV1 reporter mice and reveals TRPV1 expression in small arterioles of the ventricular myocardium where there is an analysis of whole hearts and transverse heart sections from $TRPV1^{PLAP\text{-}nLacZ}$ mice with nLacZ staining.
Figure 1D:
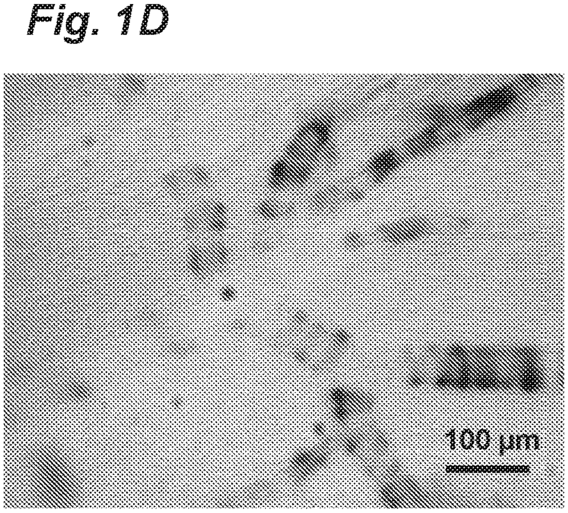
FIG. 1D is an image which shows expression of TRPV1 in TRPV1 reporter mice and reveals TRPV1 expression in small arterioles of the ventricular myocardium where there is an analysis of whole hearts and transverse heart sections from $TRPV1^{PLAP\text{-}nLacZ}$ mice with nLacZ staining.
Figure 1E:
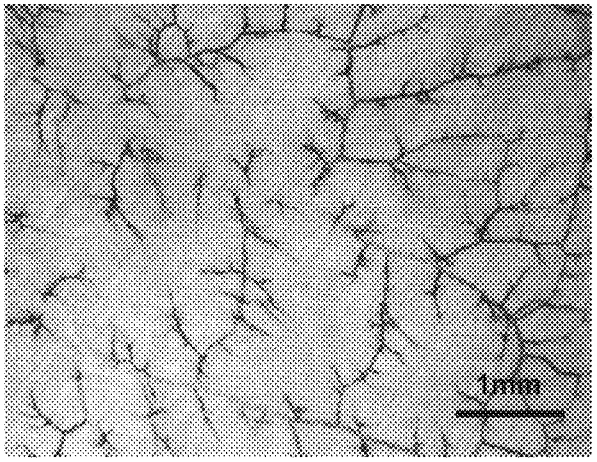
FIG. 1E is an image which shows expression of TRPV1 in TRPV1 reporter mice and reveals TRPV1 expression in small arterioles of skeletal muscle where there is an analysis of latissimus dorsi muscle from $TRPV1^{PLAP\text{-}nLacZ}$ mice with nLacZ staining.
Figure 1F:
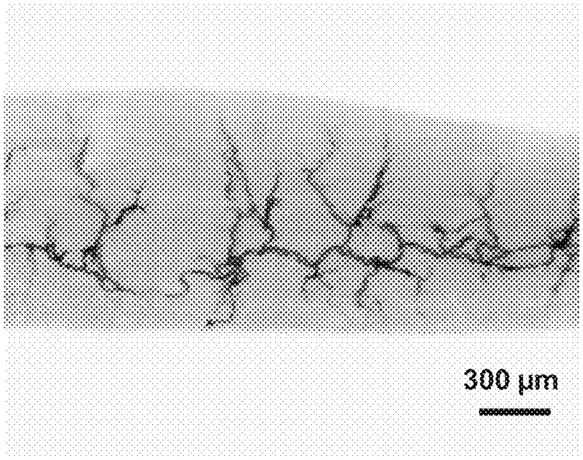
FIG. 1F is an image which shows expression of TRPV1 in TRPV1 reporter mice and reveals TRPV1 expression in small arterioles of skeletal muscle where there is an analysis of gracialis muscle from $TRPV1^{PLAP\text{-}nLacZ}$ mice with nLacZ staining.
Figure 1G:
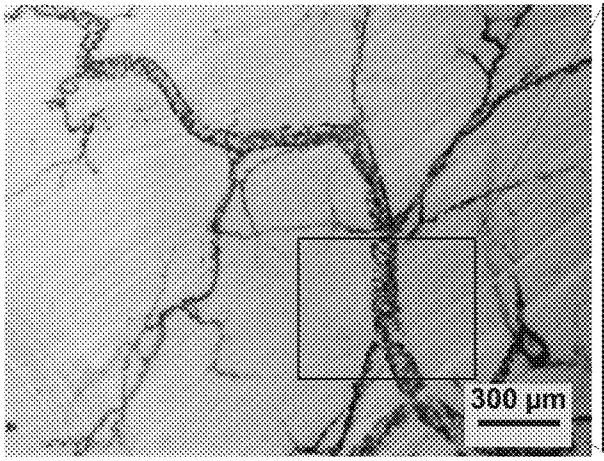
FIG. 1G is an image which shows expression of TRPV1 in TRPV1 reporter mice and reveals TRPV1 expression in small arterioles of skeletal muscle from $TRPV1^{PLAP\text{-}nLacZ}$ mice with nLacZ staining.
Figure 1H:
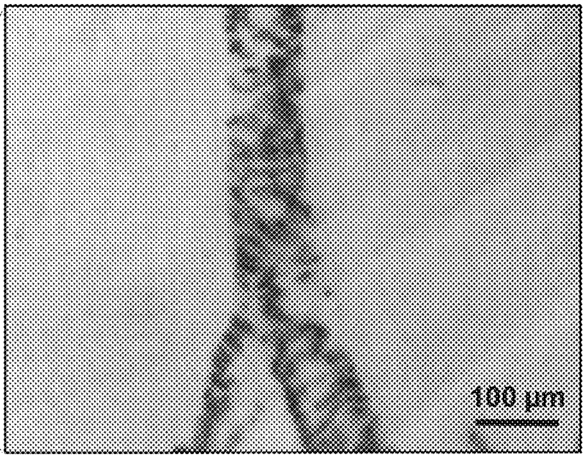
FIG. 1H is an image (magnified region of FIG. 1G) which shows expression of TRPV1 in TRPV1 reporter mice and reveals TRPV1 expression in small arterioles of skeletal muscle from $TRPV1^{PLAP\text{-}nLacZ}$ mice with nLacZ staining.

Example 1: Functional TRPV1 Resides in Vascular Smooth Muscle Cells of Muscle, Brain, and Adipose Tissues To map arterial expression of TRPV1, we exploited two validated mouse reporter lines. The first, TRPV1-Cre:tdTomato generates a very sensitive fate map of TRPV1 expression. (Mishra, S K, et al. "TRPV1-lineage neurons are required for thermal sensation. *EMBO J* 30 (2011) 582-593). The second (described in Cavanaugh, D J et al. "Trpv1 reporter mice reveal highly restricted brain distribution and functional expression in arteriolar smooth muscle cells" *J Neurosci* 31 (2011) 5067-5077). $TRPV1^{PLAP-nlacZ}$ generates expression of human placental alkaline phosphatase (PLAP) and nuclear β galactosidase (nLacZ) under the control of the endogenous TRPV1 promoter. Analysis of these mice revealed remarkable TRPV1 reporter expression specifically in vascular smooth muscle of small-diameter (<100-150 μm) arterioles of the heart, skeletal muscle and adipose tissues. In the heart, large coronary arteries were devoid of TRPV1 expression but strong tdTomato fluorescence and nLacZ staining emerged as these arteries penetrated and branched in the myocardial wall (FIG. 1A-FIG. 1D). Similarly, TRPV1 expression, though mostly absent in aorta and large trunk arteries (data not shown), erupted as arteries branched to supply skeletal muscle. Indeed, analysis of skeletal muscle revealed an abundant network of TRPV1-expressing arteries (FIG. 1E-FIG. 1F). Further, nLacZ uniformly stained vascular smooth muscle of arteries in both white and brown adipose tissue (data not shown). TRPV1 reporter expression was also detected in the cerebral circulation, including prominent labeling in the hypophyseal portal arteries and small-diameter branches of the basilar arteries. In addition, microvessels or "vasa vasorum" supplying the wall of large arteries highly expressed TRPV1. In contrast, very limited expression in arteries of other tissues examined was found including lung, kidney, liver, stomach, and intestines (data not shown). Further, despite earlier contrary findings, TRPV1 reporter expression was not detected in vascular endothelium.

Figure 2A:
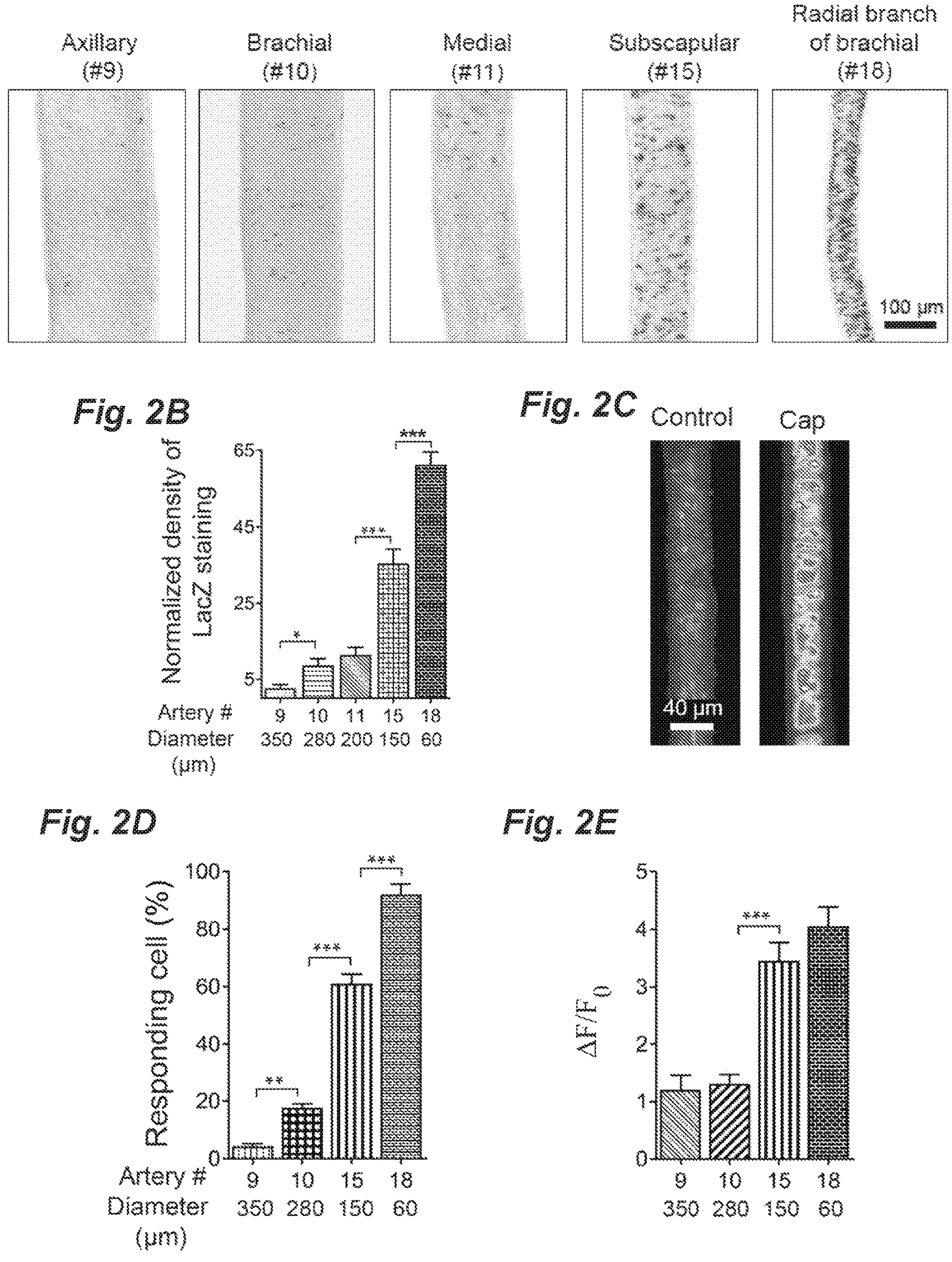
FIG. 2A is an image which shows arterial maps of functional TRPV1 expression where there is TRPV1 expression (nLacZ staining) in forelimb arteries and muscle branches versus vessel diameter (n=4-6 arteries from 5 mice per group, *P<0.05, ***P<0.001)
Figure 2F:
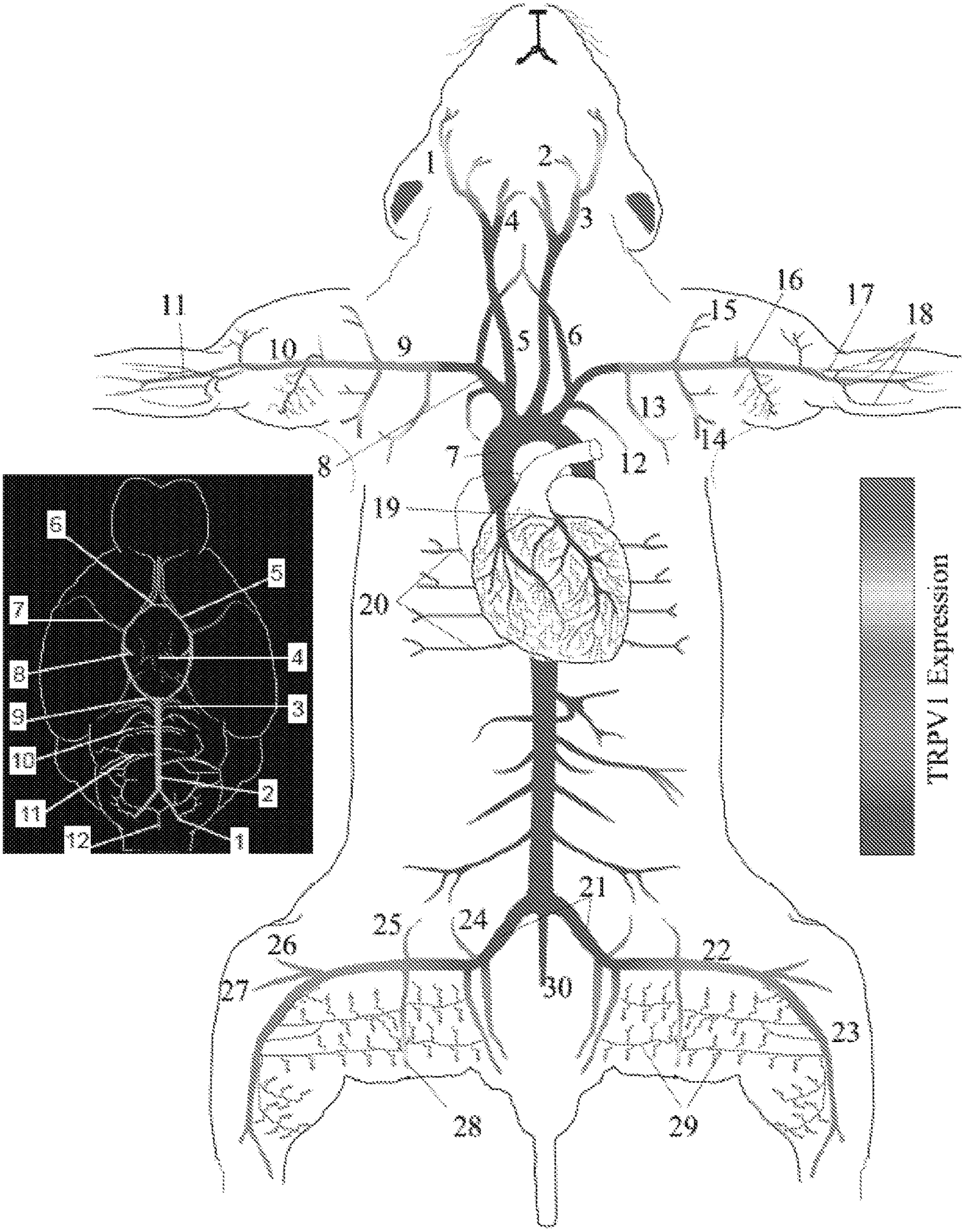
FIG. 2F is a diagram shows a heat-map of TRPV1 expression in arteries based on $TRPV1^{PLAP\text{-}nlacZ}$ mice (n≥15 mice) and confirmed by functional imaging. Inset shows the density of TRPV1 expression in cerebral arteries.

Next, to confirm that TRPV1 is functionally expressed, $Ca^{2+}$ imaging was performed in isolated arterioles and arteriolar smooth muscle (ASM) cells. The TRPV1-specific agonist, capsaicin, increased $Ca^{2+}$ signaling in a subset of ASM cells isolated from wild-type mice, whereas we observed no responses in arterioles from TRPV1-null mice. Furthermore, capsaicin sensitivity in ASM cells isolated from TRPV1-Cre:tdTomato mice was restricted to Tomato-positive cells. To confirm that the TRPV1 reporter mice accurately reflect TRPV1 protein expression, we compared capsaicin sensitivity of arteries with differential reporter expression. TRPV1 LacZ reporter expression is inversely proportional to the arterial diameter, thus arteries were isolated at different positions along the axial-brachial trunk and branches (FIG. 2A), axillary corresponding to #9 on FIG. 2F, brachial corresponding to #10 on FIG. 2F, medial corresponding to #11 on FIG. 2F, subscapsular corresponding to #14 on FIG. 2F and radial branch of the brachial artery corresponding to #18 on FIG. 2F. In response to capsaicin, the number of responsive ASM cells and the magnitude of the Ca2+ signal increased in proportion to the TRPV1 reporter signal (LacZ staining density; FIG. 2B-FIG. 2E). Similarly, capsaicin constricted coronary arterioles and the effect was inversely proportional to vessel diameter. Based on TRPV1 reporter analysis validated by functional imaging, we constructed a heat map of TRPV1 expression in the mouse arterial system (FIG. 2F). This map highlights the hierarchical distribution of TRPV1 with a concentration in small-diameter resistance arterioles of skeletal muscle, heart, and brain regions (adipose not shown). Notably, the distribution of arterial TRPV1 expression matches the classical studies mapping myogenic tone in the limb and skeletal muscle arterial tree. The areas indicated in FIG. 2F are shown in Table 1A and Table 1B below, where the relative TRPV1 expression values are shown for the vessels shown in FIG. 2F and indicated by the name of the vessel in Table 1A and 1B.

TABLE 1A

| No | Name of artery | Relative TRPV1 expression |
|---|---|---|
| 1 | Superficial temporal | *** |
| 2 | Facial | ***** |
| 3 | External carotid | ** |
| 4 | Internal carotid | ** |
| 5 | Common carotid | Nd |
| 6 | Vertebral | Nd |
| 7 | Aortic arch | Nd |
| 8 | Subclavian | * |
| 9 | Axillary | ** |
| 10 | Brachial | *** |
| 11 | Medial | *** |
| 12 | Internal mammary | ** |
| 13 | Lateral thoracic | ** |
| 14 | Subscapular | ** |
| 15 | Profunda brachii | ** |
| 16 | Ulnar collateral | ***** |
| 17 | Radial | **** |
| 18 | Radial branch of brachial | ***** |
| 19 | Coronary | Nd |
| 20 | Intercostal | ***** |
| 21 | Common iliac | Nd |
| 22 | Femoral | Nd |
| 23 | Saphenous | ** |
| 24 | Iliaco-femoral | ** |
| 25 | Superficial caudal epigastric | ** |
| 26 | Medial proximal genicular | * |
| 27 | Popliteal | * |
| 28 | Proximal caudal femoral | *** |
| 29 | Gracilis | ***** |
| 30 | Median coccygeal | Nd |

TABLE 1B

| No | Name of artery (in insert in Fig. 2F | Relative TRPV1 expression |
|---|---|---|
| 1 | Vertebral | * |
| 2 | Basilar | * |
| 3 | Superior cerebellar | *** |
| 4 | Hypophyseal portal | ***** |
| 5 | Anterior cerebral | ** |
| 6 | Anterior communicating | ** |
| 7 | Middle cerebral | Nd |
| 8 | Internal carotid | ** |
| 9 | Posterior cerebral | Nd |
| 10 | Pontine | *** |
| 11 | Anterior inferior cerebellar | ** |
| 12 | Anterior spinal | ** |

Example 2: TRPV1 Regulates Arterial Tone and Systemic Blood Pressure

To identify a physiological role for vascular TRPV1, contractility was studied in isolated pressurized arteries. Capsaicin (1 μM) constricted brain arterioles isolated from wild-type and TRPV1-Cre:tdTomato mice (by ~75% of the maximal response to 50 mM KCl; FIG. 3A-FIG. 3B), but did not constrict arteries from TRPV1-null mice. In agreement with well-studied TRPV1 pharmacology, prolonged application of capsaicin evoked a slowly declining or "desensitizing" response whereas the ultra-potent agonist, resiniferatoxin, produced a non-desensitizing response. (Resiniferatoxin is a naturally occurring chemical found in resin spurge, a cactus-like plant commonly found in Morocco, and in *Euphorbia poissonii* found in northern Nigeria, and it is a potent functional analog of capsaicin). However, the rate of capsaicin-induced desensitization in arterioles was an order of magnitude slower than responses observed in sensory nerves, indicating that arterial TRPV1 is relatively resistant to this form of inactivation.

Next, to measure the in vivo functionality of arterial TRPV1, intravital imaging of radial branch arteries was performed. Local administration of capsaicin constricted these arteries (>90%) without affecting nearby veins, or arteries in TRPV1-null mice (FIG. 3C-FIG. 3D). As an additional test of functional arterial TRPV1 expression, mice were generated expressing channelrhodopsin-2 (ChR2) under the control of TRPV1 gene regulatory elements (TRPV1-Cre:ChR2/tdTomato mice) to enable photo-control of cells expressing TRPV1. Blue light rapidly and reversibly constricted arteries in these animals, in both ex vivo and in vivo preparations, without affecting the caliber of the veins (FIG. 3A, FIG. 3B, FIG. 3D).

Next, TRPV1 contribution to myogenic tone was tested. The TRPV1 antagonist, BCTC, rapidly dilated arteries in vivo (by ~40%) and ex vivo pressurized arteries (by ~25%) (FIG. 3E-FIG. 3H), suggesting a role for TRPV1 in the maintenance of myogenic tone in these arteries. BCTC has the chemical formula: $C_{20}H_{25}ClN_4O$ and CAS #393514-24-4. Further, consistent with the TRPV1 expression pattern, BCTC had a greater dilatory effect in small diameter (~20 μm) compared with medium diameter (~60 μm) arteries (~80% versus 40%, P<0.001). This analysis revealed that TRPV1 contributes between 65-80% of total smooth muscle tone in these arteries. In contrast, BCTC had no effect in TRPV1-null arteries, confirming a selective action of this drug at TRPV1 (FIG. 3F, FIG. 3H). Systemic administration of the ganglionic blocker, hexamethonium, did not alter the diameter of small muscle arteries (data not shown), consistent with results of an earlier study. Additionally, BCTC did not inhibit norepinephrine-evoked $Ca^{2+}$ responses in ASM cells in skeletal muscle arteries (data not shown), indicating that TRPV1 is not coupled to alpha-adrenergic signaling in this tissue. These data therefore, reveal a fundamental role for TRPV1 in regulating vascular myogenic tone.

Blood flow through skeletal muscle, myocardium, brain and adipose tissues combined, represents a sizeable fraction of cardiac output, hence, TRPV1 receptors are well situated to influence systemic blood pressure. Indeed, intravenous administration of capsaicin (4-32 μg/kg) provoked marked, dose-dependent increases in systolic and diastolic blood pressure in rats, with an approximate 60 mm Hg rise observed at the highest dose tested (P<0.001; FIG. 4A, FIG. 4B, FIG. 4D). Conversely, inhibition of TRPV1 by BCTC (1 mg/kg) significantly decreased the mean arterial pressure by up to 25 mm Hg (FIG. 4C & FIG. 4E, P<0.001). The peak responses to both capsaicin and BCTC occurred without any significant changes in heart rate (FIG. 4D, FIG. 4E). However, bolus injections of capsaicin or BCTC provoked a transient bradycardic effect (data not shown), consistent with the Bezold-Jarisch reflex. This effect was prevented by atropine pretreatment (data not shown) or by slower drug infusion (FIG. 4A). FIG. 4F-4I show blood pressure changes and heart rate in wild-type and TRPV1-null mice in response to IV infusion (20 or 60 s) of capsaicin, lysophosphatidic acid, BCTC, and sodium nitroprusside (SNP) (n=3-4, P<0.01, *P<0.001). Similar pressor and depressor effects of capsaicin and BCTC were observed, respectively in wild type but not TRPV1-null mice (FIG. 4F-FIG. 4I); demonstrating that these drugs act selectively via TRPV1. Furthermore, we tested lysophosphatidic acid (LPA, C18:1), a vasoconstrictor lipid generated by platelets and atherogenic plaques, and a full TRPV1 agonist. LPA signals via a family of GPCRS receptors ($LPA_{1-6}$), but the principal LPA receptors in vascular smooth muscle are dispensable for its hypertensive effects. Notably, LPA increased blood pressure in a TRPV1-dependent manner (FIG. 4F). This finding agrees with the observation that LPA exerts a pressor effect in several mammals (cats, rats, and guinea pigs) but notably not in rabbits which possess a hypofunctional TRPV1 channel. In summary, these data show that TRPV1 contributes to systemic blood pressure, by regulating myogenic tone and sensitivity to LPA.

Example 3: TRPV1 Confers Dynamic Hyperemia

Following interruptions in blood flow, arterioles dilate to compensate the deficit in tissue perfusion. Although the underlying mechanisms for this reactive hyperemia are unclear, we found a critical role for TRPV1. In wild-type mice, application of KCl for 40 seconds (s), constricted arteries followed by a rebound dilation (of approximately 40%) that gradually returned to baseline within 60 seconds (FIG. 5A-FIG. 5C). In contrast, pretreatment with BCTC dilated the vessels precluding the post-KCl dilation and fully preventing the recovery of arterial tone (FIG. 5B, FIG. 5C).

Further, disruption of TRPV1 gene expression reduced the amplitude of the dilation and markedly prolonged the recovery (Ti/2=300 s, FIG. 5A-C; P<0.001), indicating that only minimal compensation occurs upon the loss of TRPV1. Hyperemia following a 40 s arterial constriction may reflect both myogenic and metabolic pathways.

However, we observed similar arterial dilations after brief (4-6 s) constrictions evoked by either KCl or bluelight pulses in TRPV1-Cre:ChR2 mice (FIG. 5D-FIG. 5G), supporting a primary role for a myogenic mechanism.

Furthermore, both the magnitude of the dilation and the speed of recovery were approximately two-fold greater in small diameter (~20 μm) compared to medium diameter (~60 μm) arterioles consistent with higher TRPV1 expression in the small arterioles. Additionally, after arteries were maximally dilated with a zero $Ca^{2+}$ buffer, tone returned threefold faster in wild-type mice compared to TRPV1-null mice (FIG. 5H, FIG. 5I). Collectively, these data suggest that arterial constriction and a fall in transmural pressure rapidly deactivates TRPV1 to promote arterial dilation. Subsequently, upon dilation, TRPV1 reactivates to facilitate the restoration of tone.

Example 4: a Heat-Sensitive, PLC-Diacylglycerol Pathway Underlies Stretch-Evoked Activation of TRPV1

To explore whether stretch-mediated activation of TRPV1 is cell autonomous, we studied mechanosensing in isolated ASM cells. Consistent with an earlier report, we found that hypo-osmotic stretch rapidly increased intracellular [$Ca^{2+}$] in ASM cells from wild-type mice (FIG. 6A, FIG. 6B). In contrast, stretch evoked $Ca^{2+}$ signals were significantly smaller and slower in ASM cells treated either with BCTC or isolated from TRPV1-null mice (FIG. 6A, FIG. 6B, peak rise P<0.001). Similarly, stretch rapidly altered cell morphology (constriction and membrane blebbing) selectively in the TRPV1+ population of ASM cells isolated from TRPV1-Cre:tdTomato mice (data not shown). Notably, reducing the temperature from 32° C. to 23° C. abolished stretch-evoked $Ca^{2+}$ signaling in ASM cells (FIG. 6C). Mechanoactivation of GPCRs occurs at room temperature and therefore the strict temperature dependence for mechanotransduction is consistent with the thermosensitive properties of TRPV1 in which warm thermal stimuli allosterically enhance ion channel gating.

Next, we explored the underlying mechanism for stretch-induced activation of TRPV1. Although not intrinsically mechanosensitive, TRPV1 is activated or sensitized by PLC-dependent signaling. Indeed, both PLCβ1 and PLCγ1 isoforms are known to be implicated in membrane stretch and the generation of myogenic tone. We found that the PLC inhibitor, U73122 (CAS No: 112648-68-7), topically administered to arteries in vivo, decreased tone to a similar extent as BCTC (FIG. 6D, FIG. 6E). PLC cleaves PIP2 to form diacylglycerol (DAG). In turn, DAG can activate/sensitize TRPV1 channels either directly or via PKC-dependent phosphorylation. However, the PKC inhibitors GF 109203X (2-[1-(3-Dimethylaminopropyl)indol-3-yl]-3-(indol-3-yl) maleimide, CAS NO: 133052-90-1) and chelerythrine chloride (1,2-dimethoxy-12-methyl-[1,3]benzodioxolo[5,6-c] phenanthridin-12-ium;chloride: CAS NO: 3895-92-9) did not alter tone or post-constriction dilation (FIG. 6E), indicating a nonessential role for PKC. In contrast, the membrane permeable analog of DAG, 1-Oleoyl-2-acetyl-sn-glycerol (OAG), reversibly constricted arteries and restored arterial tone after inhibition of PLC in a TRPV1-dependent manner (FIG. 6D & FIG. 6E). Moreover, inhibiting DAG lipase, the major enzyme responsible for DAG/OAG metabolism, with RHC80267 (cyclohexylideneamino)N-[6-[(cyclohexylideneamino)oxycarbonylamino]hexyl]carbamate, CAS NO: 83654-05-1) increased the responses to OAG, thus, ruling out a role for OAG metabolites.

RHC80267 alone partially constricted arteries (P<0.01), which is consistent with an accumulation of endogenous DAG acting at TRPV1. Thus, PLC signalling and generation of DAG appears to couple membrane stretch to activation of TRPV1, and this occurs in a temperature-dependent manner. These findings agree with biochemical studies of others showing that arterial stretch (60 & 120 mm Hg) generates a graded increase in DAG within ASM cells.

Finally, nifedipine (CAS NO: 21829-25-4) fully dilated arterioles consistent with an essential role for L-type Ca2+ channels in generating a resting arteriole tone (FIG. 6F). In contrast, nifedipine only partly inhibited capsaicin-evoked constriction, indicating that Ca2+ influx alone via fully activated TRPV1 channels is sufficient to constrict arteries. FIG. 6G summarizes the proposed signaling cascade for the generation of TRPV1-dependent myogenic tone, and highlights signaling intermediaries that have been experimentally validated to be essential (underlined) or non-essential (bold and italics).

Example 5: Use of TRPV1 Agonists Stabilize Blood Pressure in an LPS-Induced Sepsis Model As previously shown and further confirmed, $TRPV1^{PLAP-nlacZ}$ mice were used to map TRPV1 expression in the entire arterial system of the mouse. The data showed striking TRPV1 expression in small arteries supplying skeletal muscle, heart, fat and a subset of the brain vasculature. TRPV1 mRNA in small arteries is ~15% of dorsal root ganglion (DRG) levels. Mapping was validated by correlating the nLacZ signal with functional responses (electrophysiology and $Ca^{2+}$ imaging) to the TRPV1 agonist, capsaicin. Further, capsaicin constricted small arteries ex vivo and in vivo (FIG. 7A-FIG. 7C) and markedly increased systemic blood pressure (BP) in mice (FIG. 8-FIG. 10). As shown in FIG. 8, capsaicin-evoked pressor effect does not exhibit tachyphylaxis. Repeated injections of capsaicin produce similar increases in BP. Non-desensitizing currents in a voltage-clamped vascular smooth muscle cell are shown. As shown in FIG. 8, capsaicin infusion produces a sustained increase in BP. As shown in FIG. 10, LPA infusion induces a sustained rise in systemic BP.

The present results provide mechanistic explanations of observations in previous studies of experimentally induced sepsis in TRPV1-null mice, which exhibited both a greater fall in BP and higher mortality than their wild-type counterparts (Clark, N., et al. "The transient receptor potential vanilloid 1 (TRPV1) receptor protects against the onset of sepsis after endotoxin. *FASEB Journal* 21 (2007) 3747-3755; Fernandes, E S, et al. TRPV1 deletion enhances local inflammation and accelerates the onset of systemic inflammatory response syndrome. *Journal of immunology* 188 (2012) 5741-5751; Guptill, V., et al. "Disruption of the transient receptor potential vanilloid 1 can affect survival, bacterial clearance, and cytokine gene expression during murine sepsis" *Anesthesiology* 114 2011)1190-1199; Wang, Y., et al. "TRPV1-mediated protection against endotoxin-induced hypotension and mortality in rats" *American Journal of Physiology: Regulatory, integrative and comparative physiology* 294 (2008) R1517-1523).

The present studies support and provide methods of ameliorating hypotension in septic shock through the use of TRPV1 agonists. In certain embodiments, working doses established initially in urethane-anesthetized mice are tested in conscious animals. Mice are surgically implanted with in-dwelling jugular catheters by which drugs are perfused 48 h later. BP measurements are accomplished by tail-cuff plethysmography and made (at 5 min intervals) before and after lipopolysaccharide (LPS) treatment and during 30-60 min infusion of TRPV1 agonists. In one model of septic shock, LPS is administered at 10 mg/kg, IV. Thereafter, treatment is instituted with one of the following TRPV1 agonists: (i) Capsaicin (10-40 g/kg/min), the prototypic agonist of TRPV1, which has a short in vivo half-life of 3-5 minutes; (ii) BrP-LPA (2-10 μg/kg/min), a structural analog of lysophosphatidic acid (LPA) that activates TRPV1 with a similar potency/efficacy but that is also is an antagonist of most LPA receptors (LPA1-LPA4). This dose is 10% of the LPA dose based on the stability and our preliminary data; (iii) Double-knot spider toxin, (DkTx), which is a 79 a.a. peptide derived from the venom of the tarantula species *Ornithoctonus huwena* (a.k.a. Earth Tiger). DkTx is highly selective for TRPV1, locking the channel open with very slowly reversibility. DkTx (20-2000 ng/kg) is injected using an escalating dose regimen to effect.

Previous studies have shown that LPS produces a marked hypotension (~50-60 mmHg) that persists for several hours (Ueno et al. "Comparative study of endotoxin-induced hypotension in kininogen deficient rats with that in normal rats. *British Journal of Pharmacology* 114 (1995)1250-1256). In one embodiment, an endpoint is normalization of BP over a 30-60 minute period by titrated infusion of the TRPV1 agonists. Our preliminary data show that capsaicin produces a persistent increase in BP over 15-30 minutes although any desensitization occurring in a given animal species over the 60-minute period will be taken in to account in determining effectiveness and need for further infusion. In one embodiment, BrP-LPA activates TRPV1 with little to no desensitization to achieve a more sustained pressor effect. In addition to its pressor action, BrP-LPA has the advantage of being anti-coagulant (by antagonizing LPA receptors), and is expected to satisfy this further requirement in the context of sepsis. In another embodiment, DkTx activates TRPV1 with little to no desensitization to achieve a more sustained pressor effect. The high avidity of DkTx at TRPV1 offers the potential for very selective agonism of TRPV1 with minimal CNS effects. TRPV1 agonists may trigger pain responses due to activation of sensory nerves, thus, in certain embodiments, pain control is effected by an initial slow to very slow infusion rate, which will limit sensory nerve activation (due to desensitization of TRPV1, as would be the case for capsaicin, or alternatively via depolarization block, as would be the case for DkTx).

It is noted that the slow infusion approach is employed and is accepted practice during infusions of $MgSO_4$ in humans. There is one previous study in humans describing the effects of IV capsaicin. In response to bolus administration of capsaicin (up to 4 μg/kg), subjects reported a mild burning sensation and a feeling of warmth (Winning et al., 1986). It is expected that TRPV1 agonists can be systemically administered to humans (albeit with slow infusion) with minimal accompanying pain responses.

Example 6: Limiting Toxicity to Sensory Nerves with Systemic Administration

A potential adverse effect of TRPV1 agonists is toxicity to sensory nerves. Indeed, in vivo administration of the ultra-potent agonist, resiniferatoxin (RTX), or even high doses of capsaicin can lead to destruction of TRPV1+ neurons (Szallasi S and Blumberg P M, "Vanilloid receptor loss in rat sensory ganglia associated with long term desensitization to resiniferatoxin" *Neurosci Lett* 140 (1)(1992)51-54. In one embodiment, TRPV1 agonists that poorly penetrate the CNS, such as DkTx or BrP-LPA, are employed. In vivo toxicity is tested by the administration of TRPV1 agonists in $TRPV1^{PLAP\text{-}nLacZ}$ mice based on the highest cumulative doses utilized in EXAMPLE 5. One week later, DRG are isolated and analyzed for nLacZ staining. Our preliminary data show that RTX (50 μg/kg) nearly completely abolishes nLacZ staining in DRG (FIG. 11). This analysis therefore determines TRPV1 agonist neurotoxicity and forms an assay for toxicity limiting strategies. In one embodiment, BrP-LPA is employed as a more hydrophilic molecule than capsaicin with less neurotoxicity. In another embodiment, DkTx, with limited CNS penetration, is employed to avoid neurotoxicity.

Materials and Methods

Animals: All experimental procedures involving mice and rats were approved by the Georgetown University Animal Care and Use Committee and the Ethics Committee on Animal Research of the University of Debrecen. Both Wistar rats (250-450 g) and C57B1 mice (20-30 g) were housed at 24-25° C. and had ad libitum access to a standard laboratory chow and water.

Mouse lines. The TRPV1-Cre transgenic mouse line (donated by Dr. Mark Hoon, NIH) was created using a BAC transgene containing the entire TRPV1 gene/promoter (50 kbp of upstream DNA) and IRES-Cre-recombinase. (Mishra, S K, et al. supra). Importantly, Cre expression in this mouse faithfully corresponds with the expression of endogenous TRPV1. The TRPV1-Cre (hemizygous) mice were crossed with ai9 ROSA-stop-tdTomato mice (The Jackson Laboratory). The $TRPV1^{PLAP\text{-}nlacZ\ mice}$ (Jackson Laboratory) were developed by Allan Bausbaum and colleagues (UCSF) to express human placental alkaline phosphatase (PLAP) and nuclear lacZ under the control of the TRPV1 promoter. See Cavanaugh, D J et al, supra). The targeting construct contains an IRES-PLAP-IRESnlacZ cassette immediately 3' of the TRPV1 stop codon, which permits the transcription and translation of PLAP and nlacZ in cells expressing TRPV1 without disrupting the TRPV1 coding region. TRPV1-null mice were purchased from The Jackson Laboratory. TRPV1-Cre:ChR2/tdTomato mice were generated by crossing TRPV1-Cre mice with ChR2/tdTomato mice (The Jackson Laboratory).

X-gal staining. $TRPV1^{PLAP\text{-}nlacZ}$ mice were anesthetized with isoflurane and perfused through the heart using PBS (0.1M, pH 7.3) followed by ice-cold 2-4% buffered paraformaldehyde. Whole skinned mice, brains, hearts, and trunk arteries were dissected and post-fixed in 2-4% buffered paraformaldehyde on ice for 90 min, after which they were washed in PBS (containing 5 mM EGTA and 2 mM $MgCl_2$; 0.1M, pH 7.3) on ice and stained in X-gal solution [containing 1 mg/ml X-gal, 5 mM $K_3Fe(CN)_6$, 5 mM $K_4Fe(CN)_6$, 0.01% deoxycholate, and 2 mM $MgCl_2$ in PBS; 0.1M, pH 7.3] at 37° C. overnight. nLacZ staining was imaged in situ, in heart sections (120-150 μm thick) and in isolated arteries. To calculate the density of the signal, defined arteries and arterioles were isolated from $TRPV1^{PLAP\text{-}nlacZ}$ and wild-type mice, stained and photographed in parallel. Densitometry was performed with ImageJ to yield density in arbitrary units (normalized to the wild-type signal). To map arterial/arteriole TRPV1 expression, we compared the density of X-gal staining in main trunk arteries and tributaries, heart and brain. The distribution of intensities revealed 5 broad peaks (a baseline and four positive peaks, for example see FIG. 2*b*) that were color-coded from zero (dark blue) to a maximum (red).

Arterial smooth muscle cell isolation. Radial artery branch (artery #18) and cerebellar branch (cerebral artery #3) were washed in $Mg^{2+}$-based physiological saline solution (Mg-PSS) containing 5 mM KCl, 140 mM NaCl, 2 mM $MgCl_2$, 10 mM Hepes, and 10 mM glucose, (pH 7.3). Arteries were initially digested in papain (0.6 mg/ml) (Worthington) and dithioerythritol (1 mg/ml) in Mg-PSS at 37° C. for 15 min, followed by a 15-min incubation at 37° C. in type II collagenase (1.0 mg/ml) (Worthington) in Mg-PSS. The digested arteries were washed three times in ice-cold Mg-PSS solution and incubated on ice for 30 min. After this incubation period, vessels were triturated to liberate smooth muscle cells and stored in ice-cold Mg-PSS before use. Smooth muscle cells were studied within 6 hours of isolation.

$Ca^2$ imaging. Arterioles and ASM cells were loaded with 1 μM Fluo-4-AM (Invitrogen, Thermo Fisher Scientific) in a standard buffer containing in mM: 140 NaCl, 4 KCl, 1 $MgCl_2$, 1.2 $CaCl_2$), 10 HEPES, and 5 glucose (pH 7.3). For studies of hypoosmotic stretch, NaCl was reduced to 70 mM, and mannitol (70-150 mM) was added to adjust osmolarity to between 220 and 310 mOsm. Final osmolarity was confirmed with an osmometer (Model 3320, Advanced Instruments). Temperature was maintained either at room temperature (23° C.) or at 32-35° C. using a heated microscope stage (Tokai Hit). Bath temperature was verified by a thermistor probe (Warner Instruments). Cells were imaged with a 20× objective using a Nikon TE2000 microscope with an excitation filter of 480±15 nm and an emission filter of 535±25 nm. The images were captured by a Retiga 3000 digital camera (QImaging) and analysis was performed offline using ImageJ. Individual smooth muscle cells were counted for sensitivity to capsaicin and KCl. Sensitivity was defined as a greater than 20% change from baseline (typically responses were greater than 100%). Solutions were applied via a pencil (250-μm diameter) that was attached to a valve-controlled gravity-fed perfusion system.

Ex vivo artery physiology: Skeletal muscle arteries (radial artery branch, artery #18, subscapular branch artery #14) and cerebellar branch, cerebral artery #3) were isolated and cannulated with glass micropipettes secured with monofilament threads. The pipette and bathing solution contained modified PSS (125 mM NaCl, 3 mM KCl, 26 mM $NaHCO_3$, 1.25 mM $NaH_2PO_4$, 1 mM $MgCl_2$, 4 mM D-glucose, and 2 mM $CaCl_2$)) aerated with a gas mixture consisting of 95% 02, 5% $CO_2$, to maintain pH (pH 7.4). Arterioles were pressure clamped (60 mmHg) using a custom-built apparatus in a heated imaging chamber (Tokai Hit), viewed with a 10× objective using a Nikon TE2000 microscope and recorded by a Retiga 3000 digital camera (QImaging). The arteriole diameter was measured at several locations along each arteriole using the NIH-ImageJ software's edge-detection plug-in (Diameter). The software automatically detects the distance between edges (by resampling a total of five times from adjacent pixels) yielding a continuous read-out SD of a vessel's diameter.

Intravital imaging: Intravital imaging was performed in radial artery branches (~20 and 60 μm in diameter, artery #18 in FIG. 2F). Animals were anesthetized with urethane (1.2 g/kg/IP). The forelimb was shaved and an incision was made. The skin and underlying muscle tissue were reflected to expose the brachial-radial artery junction. Both in WT and TRPV1-null mice, the arteries were visualized with a Zeiss stereomicroscope and illuminated with a low power blue light (using a standard GFP filter cube) exploiting the differential auto-fluorescence between tissue and blood. In TRPV1-Cre:ChR2/tdTomato mice, arteries were visualized with low power visible irradiation and stimulated with blue light. The exposed arteries were locally perfused (using a 250 μm pencil connected to a valve-controlled gravity-fed perfusion system) with preheated PSS solutions containing in mM: 140 NaCl, 4 KCl, 1 $MgCl_2$, 1.2 $CaCl_2$), 10 HEPES, and 5 glucose (pH 7.3). The surface tissue temperature (34-35° C.) was measured via a thermistor (Warner Instruments) that was positioned next to the artery. Arteries were challenged with a PSS containing 0 $Ca^{2+}$/1 mM EGTA to measure the passive diameter. The arteriole diameter was measured using ImageJ as described above for the ex vivo vessels.

Systemic blood pressure recording: The experiments were performed in anesthetized mice (urethane 1.2-1.5 g/kg/IP) and rats (thiopental 50 mg/kg/IP; supplement if needed was 5 mg/kg/IV). Subsequent to anesthesia, mice or rats underwent cannulation of the carotid artery and jugular vein as follows:

Surgical preparation mouse: After the depth of anesthesia was confirmed by lack of pedal and corneal reflexes, mice were intubated via the trachea after a tracheotomy to maintain an open airway and to institute artificial respiration when necessary. Next, the left carotid artery and the right jugular vein were cannulated with a Millar catheter (1F SPR-1000) and a polyethylene tubing (PE-10), respectively, for monitoring blood pressure and for systemic infusion of drugs. To monitor heart rate, a three-point needle electrode-assembly representing Lead II of the electrocardiogram (ECG) was attached subcutaneously to the right and left forelimbs along with a reference electrode to the left hindlimb. Both the Millar catheter and the ECG assembly were coupled to a PowerLab data acquisition system (ADInstruments, Inc.). Prior to vessel cannulation, the adjacent left cervical vagus was carefully isolated from the left carotid artery. Body temperature was monitored by a digital rectal thermometer and maintained at 37±1° C. with an infrared heat lamp.

Surgical preparation rat: Similar to the mouse, following intubation of the trachea, the left carotid artery, and jugular vein were cannulated with a polyethylene tubing (PE50) to monitor blood pressure and infuse drugs, respectively. Blood pressure was continuously recorded via a pressure transducer connected to the Haemosys hemodynamic system (Experimetria Ltd., Budapest, Hungary), as was the ECG. The ECG was recorded from the extremities of the animal by means of hypodermic metal needles inserted subcutaneously in accordance with the Einthoven method (I, II, III leads). As in the mouse, heart rate was determined from lead II of the ECG recordings and body core temperature was maintained at 37±0.5° C. with a temperature controlled infrared heating lamp. Drug administration: Intravenous infusion of drugs was initiated only when a stable baseline of blood pressure and heart rate was present. This was also the case when drugs were re-administered.

Chemicals. Capsaicin, resiniferatoxin (RTX) and BCTC were purchased from Tocris Bioscience or Adooq Bioscience and stock solutions were prepared in EtOH at 1 M and 100 mM, respectively. 1-Oleoyl-2-acetyl-sn-glycerol, U73122, U73343 and RHC80267 were purchased from Cayman Chemical. Unless otherwise indicated, all other chemicals were obtained from Sigma-Aldrich (St. Louis, MO). Final EtOH concentration of the drug solutions administered to each animal was <0.1%.

Statistical analysis: Data were analyzed using Prism (GraphPad Software, La Jolla, CA) and are expressed as means+SEM. Unless otherwise stated, statistical significance was evaluated using one-way ANOVA with treatment interactions assessed by Tukey's post hoc multiple comparisons test.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A method of treatment of hypotension in a human patient in septic shock, the method comprising: co-administering at least two TRPV1 agonists to the patient in an amount sufficient to increase and/or maintain a systolic blood pressure of 65 mm Hg or greater in the patient, wherein the at least two TRPV1 agonists comprise BrP-LPA and a vanillotoxin.

2. The method of claim 1, wherein the at least two TRPV1 agonists further comprise one or more of a TRPV1 agonist selected from the group consisting of a capsaicin, a daphnane TRPV1 agonist, N-oleoyl dopamine, N-arachidonyl dopamine.

3. The method of claim 2, wherein the TRPV1 agonist is a capsaicin analogue selected from the group consisting of oleoylvanillamine, rinvanil, and phenylacetylrinvanil.

4. The method of claim 2, wherein the vanillotoxin is a double-knot spider toxin (DkTx).

5. The method of claim 2, wherein the TRPV1 agonist is a daphnane TRPV1 agonist selected from the group consisting of resiniferatoxin and tinyatoxin.

6. The method of claim 1, wherein the at least two TRPV1 agonists are co-administered with an adrenergic agonist selected from the group consisting of dopamine, phenylephrine, norepinephrine, and metaraminol.

7. The method of claim 1, wherein the at least two TRPV1 agonists are co-administered with an angiotensin.

8. The method of claim 7, wherein the angiotensin is selected from the group consisting of Angiotensin II (SEQ ID NO. 1), Angiotensin III (SEQ ID NO. 2) and Angiotensin IV (SEQ ID NO. 3).

9. The method of claim 1, wherein the at least two TRPV1 agonists are administered intravenously.

10. The method of claim 1, wherein the at least two TRPV1 agonists are administered by a topical patch.

11. The method of claim 1, wherein the at least two TRPV1 agonists are co-lyophilized prior to treatment.

12. The method of claim 1, wherein the vanillotoxin is a double-knot spider toxin (DkTx).

13. The method of claim 1, wherein the at least two TRPV1 agonists further comprise one or more of a TRPV1 agonist selected from the group consisting of capsaicin, oleoylvanillamine, rinvanil and phenylacetylrinvanil.

14. A pharmaceutical formulation for increasing blood pressure in a human patient in septic shock, the formulation comprising at least two TRPV1 agonists in a dosage form for parental administration, wherein the at least two TRPV1 agonists comprise BrP-LPA and a vanillotoxin.

15. The pharmaceutical formulation of claim 14, wherein the at least two TRPV1 agonists further comprise one or more of a TRPV1 agonist selected from the group consisting of a capsaicin, a daphnane TRPV1 agonist, N-oleoyl dopamine, N-arachidonyl dopamine.

16. The pharmaceutical formulation of claim 15, wherein the formulation is lyophilized.

17. The pharmaceutical formulation of claim 16, further comprising a co-lyophilized adrenergic agonist selected from the group consisting of dopamine, phenylephrine, norepinephrine, and metaraminol.

18. The pharmaceutical formulation of claim 16, further comprising a co-lyophilized angiotensin selected from the group consisting of Angiotensin II (SEQ ID NO. 1), Angiotensin III (SEQ ID NO. 2) and Angiotensin IV (SEQ ID NO. 3).

19. The pharmaceutical formulation of claim 14, wherein the vanillotoxin is a double-knot spider toxin (DkTx).

20. The pharmaceutical formulation of claim 14, wherein the at least two TRPV1 agonists further comprise one or more of a TRPV1 agonist selected from the group consisting of capsaicin, oleoylvanillamine, rinvanil and phenylacetyl-rinvanil.

* * * * *

SEQUENCE LISTING

```
<160> NUMBER OF SEQ ID NOS: 3

<210> SEQ ID NO 1
<211> LENGTH: 8
<212> TYPE: PRT
```

-continued

```
<213> ORGANISM: Artificial Sequence
<220> FEATURE:
<223> OTHER INFORMATION: Description of Artificial Sequence: Synthetic
      peptide

<400> SEQUENCE: 1

Asp Arg Val Tyr Ile His Pro Phe
1               5


<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Val Tyr Ile His Pro Phe
1               5


<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Tyr Ile His Pro Phe
1               5
```